United States Patent
Breneisen et al.

(10) Patent No.: US 11,129,577 B2
(45) Date of Patent: Sep. 28, 2021

(54) OPTICAL CANCER DETECTOR USING DEEP OPTICAL SCANNING AND MULTI LAYER NEURAL NETWORK

(71) Applicant: Telebyte, Inc., Hauppauge, NY (US)

(72) Inventors: Michael Breneisen, East Northport, NY (US); Kenneth S. Schneider, Plainview, NY (US); Joel A. Strom, Tampa, FL (US); John Murray, Centereach, NY (US)

(73) Assignee: Telebyte, INC., Hauppauge, NY (US)

( * ) Notice: Subject to any disclaimer, the term of this patent is extended or adjusted under 35 U.S.C. 154(b) by 439 days.

(21) Appl. No.: 15/274,925

(22) Filed: Sep. 23, 2016

(65) Prior Publication Data
US 2017/0007187 A1    Jan. 12, 2017

Related U.S. Application Data

(63) Continuation-in-part of application No. 14/624,190, filed on Feb. 17, 2015, now abandoned.

(51) Int. Cl.
*A61B 5/00* (2006.01)
*G16H 40/67* (2018.01)
(Continued)

(52) U.S. Cl.
CPC .......... *A61B 5/7267* (2013.01); *A61B 5/0022* (2013.01); *A61B 5/0035* (2013.01);
(Continued)

(58) Field of Classification Search
CPC .... G16H 40/63; G16H 50/20; G06F 19/3406; G06F 19/345; A61B 5/7267;
(Continued)

(56) References Cited

U.S. PATENT DOCUMENTS

| 5,123,731 | A | * | 6/1992 | Yoshinaga | G01N 15/0205 |
| | | | | | 250/461.2 |
| 5,218,529 | A | * | 6/1993 | Meyer | G06N 3/02 |
| | | | | | 700/90 |

(Continued)

FOREIGN PATENT DOCUMENTS

| WO | 2013-052318 A1 | 4/2013 |
| WO | 2013-103475 A2 | 7/2013 |

OTHER PUBLICATIONS

Bevilacqua, F. et al., Broadband Absorption Spectroscopy in Turbid Media by Combined Frequency-domain and Steady State Methods, Applied Optics, vol. 39, No. 34, pp. 6498-6507, Dec. 1, 2000.

(Continued)

*Primary Examiner* — Serkan Akar
(74) *Attorney, Agent, or Firm* — Hunton AK, LLP

(57) ABSTRACT

A device and a system, based upon Deep Optical Scanning (DEOS), for the detection of certain cancers such as breast cancer and the determination of their response to therapy. DEOS is based upon the nonlinear optical interaction of incident laser generated light with tissue. The cancers may either be subsurface or on the surface. The system includes hardware and software components that form subsystems including: an Optical Electronic Subsystem, a Digitization Subsystem, a Parameter Computation Subsystem, an Archive, an Artificial Intelligence Subsystem, and a Presentation Subsystem. The device can be made portable and is non-invasive in its application to a patient. The system can be integrated into a hybrid architecture with other imaging techniques used for the detection of cancers.

6 Claims, 21 Drawing Sheets

(51) Int. Cl.
G16H 50/30 (2018.01)
A61B 10/02 (2006.01)
G16H 40/63 (2018.01)
G16H 50/20 (2018.01)
G16H 30/40 (2018.01)
A61B 8/08 (2006.01)

(52) U.S. Cl.
CPC .......... *A61B 5/0062* (2013.01); *A61B 5/0075* (2013.01); *A61B 5/0077* (2013.01); *A61B 5/4842* (2013.01); *A61B 5/7203* (2013.01); *A61B 5/7228* (2013.01); *A61B 10/02* (2013.01); *G16H 30/40* (2018.01); *G16H 40/63* (2018.01); *G16H 40/67* (2018.01); *G16H 50/20* (2018.01); *G16H 50/30* (2018.01); *A61B 5/743* (2013.01); *A61B 8/085* (2013.01); *A61B 8/0825* (2013.01); *A61B 8/5223* (2013.01); *A61B 2562/0233* (2013.01); *A61B 2576/00* (2013.01)

(58) Field of Classification Search
CPC ... A61B 5/0077; A61B 5/7228; A61B 5/0022; A61B 5/0075; A61B 5/0062; A61B 10/02; A61B 5/0035; A61B 5/7203; A61B 8/085; A61B 8/00
See application file for complete search history.

(56) References Cited

U.S. PATENT DOCUMENTS

| | | | | |
|---|---|---|---|---|
| 5,260,871 | A * | 11/1993 | Goldberg | G06T 7/0012 600/320 |
| 5,835,901 | A * | 11/1998 | Duvoisin, III | G06K 9/627 706/16 |
| 6,004,267 | A * | 12/1999 | Tewari | A61B 5/06 600/300 |
| 8,244,332 | B2 | 8/2012 | Azar et al. | |
| 2001/0023419 | A1 * | 9/2001 | Lapointe | G16H 50/20 706/15 |
| 2002/0007122 | A1 | 1/2002 | Kaufman et al. | |
| 2003/0023172 | A1 | 1/2003 | Tromberg et al. | |
| 2003/0158829 | A1 * | 8/2003 | Kam | G06F 19/12 706/15 |
| 2004/0142496 | A1 | 7/2004 | Nicholson et al. | |
| 2004/0181375 | A1 * | 9/2004 | Szu | A61B 5/7267 703/2 |
| 2004/0242972 | A1 * | 12/2004 | Adak | G16H 50/70 600/300 |
| 2007/0092888 | A1 * | 4/2007 | Diamond | C12Q 1/6883 435/6.11 |
| 2007/0182960 | A1 | 8/2007 | Jayaraman | |
| 2008/0009748 | A1 | 1/2008 | Gratton et al. | |
| 2008/0015448 | A1 * | 1/2008 | Keely | A61B 5/0091 600/477 |
| 2008/0101657 | A1 | 5/2008 | Durkin et al. | |
| 2009/0005692 | A1 | 1/2009 | Intes et al. | |
| 2011/0194176 | A1 * | 8/2011 | Behrend | A61B 3/0008 359/387 |
| 2011/0274338 | A1 | 11/2011 | Park et al. | |
| 2011/0282166 | A1 | 11/2011 | Chen et al. | |
| 2014/0243681 | A1 | 8/2014 | Hielscher et al. | |
| 2014/0249414 | A1 | 9/2014 | Herzog et al. | |

OTHER PUBLICATIONS

Cerussi, A., et al., Predicting Response to Breast Cancer Neoadjuvant Chemotherapy Using Diffuse Optical Spectroscopy, PNAS, vol. 104, No. 10, pp. 4014-4019, Mar. 6, 2007.

Landau, H.J., Necessary Density Conditions for Sampling and Interpolation of Certain Entire Functions, Acta Mathematica, vol. 117, pp. 37-52, Jul. 1, 1967.

Roblyer, D. et al., Feasibility of Direct Digital Sampling for Diffuse Optical Frequency Domain Spectroscopy in Tissue, Measurement Science and Technology, vol. 24, pp. 1-9, Mar. 7, 2013.

Nachabe, R. et al., Diagnosis of breast cancer using diffuse optical spectroscopy from 500 to 1600 nm: a comparison of classification methods, Aug. 16, 2011, p. 5, paragraph 2; p. 6, section 2.1; p. 7, section 2.2.

Meir, A. et al., "Distributed network, wireless and cloud computing enabled 3-D ultrasound: a new medical technology paradigm," PLoS ONE Journal, Nov. 19, 2009, pp. 2-6.

Stantchev, V. et al., "Cloud computing based systems for healthcare," The Scientific World Journal, Apr. 15, 2014, figure 5, section 3.2.

International Search Report and Written Opinion from PCT/US2016/17804, dated Apr. 29, 2016.

Matousek, P. et al., "Emerging concepts in deep Raman spectroscopy of biological tissue", Analyst, 2009, 134, 1058-1066 (first published online Feb. 17, 2009)—Abstract only.

Yadav et al., "Mitochondrial DNA mutations and breast tumorigenesis", Biochim Biophys Acta. Dec. 2013; 1836 (2): 336-344, doi:10.1016/j.bbcan.2013.10.002.

Keikhosravi et al., "Second-harmonic generation imaging of cancer", Methods in Cell Biology, vol. 123 (2014), Chapter 28, pp. 531-546.

Adur et al., "Optical Biomarkers of Serous and Mucinous Human Ovarian Tumor Assessed with Nonlinear Optics Microsopies", Oct. 8, 2012, http://dx.doi.org/10.1371/journal.pone.0047007.

Hu et al., "Nonlinear Optical Microscopy for Histology of Fresh Normal and Cancerous Pancreatic Tissues", May 24, 2012, http://dx.doi.org/10.1371/jounal.pone.0037962.

Le et al., "Nonlinear Optical Imaging to Evaluate the Impact of Obesity on Mammary Gland and Tumor Stroma" Molecular Imaging, vol. 6, No. 3 (May-Jun. 2007): pp. 205-211; and Supplementary information (4 pages).

* cited by examiner

OPTICAL CANCER DETECTOR USING DEEP OPTICAL SCANNING AND MULTI LAYER NEURAL NETWORK

CROSS-REFERENCE TO RELATED APPLICATIONS

This application is a continuation-in-part of U.S. patent application Ser. No. 14/624,190, filed Feb. 17, 2015, which is herein incorporated by reference in its entirety.

FIELD OF THE INVENTION

The present invention relates to devices that use imaging techniques for the detection of certain subsurface and surface cancers, such as breast cancer, and the assessment of their response to therapy.

BACKGROUND INFORMATION

Cancer is a major cause of morbidity and mortality in the United States, and will be more so with the aging of the population. Early detection and classification of malignant tumors combined with accurate assessment of their response to therapy could have important implications, not only for patient care, but also from the public health and economic perspectives. Of particular interest is breast cancer, where malignant tumors may occur anywhere from on the surface to deep within the breast. In addition to surgical excision, treatment often involves multimodality therapeutics, including radio-, chemo-, and immuno-therapies. The immediate concerns of the treating physician are to be able to correctly diagnose a suspected tumor in order to commence targeted therapy and rapidly determine the patient's therapeutic response.

A number of techniques are currently employed to screen patients for breast cancer. For example, breast cancer screening employs mammography, magnetic resonance imaging (MM), ultrasonography, thermography, and irradiation by microwaves. However, mammography requires compression of the breast, which is often uncomfortable for the patient. Mammography also exposes the patient to ionizing radiation and may fail to detect malignant tumors in some patients, especially younger individuals such as those less than 50 years old, and those with dense breast tissue. Most guidelines do not recommend routine mammography for such patients because of concerns regarding the effects of radiation exposure and false positive identification rates. MRI requires an intravenous contrast injection or confining the patient to an enclosed space. Also, mammography, MRI, ultrasonography, and microwave imaging cannot be performed in a primary care physician's office or at Critical Care Clinics (CCCs).

Diffuse Optical Spectroscopy (DOS) is a proposed method to determine the presence of breast cancer tumors and to track the response of breast cancer to therapies. DOS has considerable advantages over the approaches mentioned above. For example, DOS does not present the discomfort associated with mammography. Because DOS is based upon the scattering of coherent, laser generated light, it does not present any risk of exposing the patient to ionizing radiation. However, DOS is typically only applicable when the suspected neoplastic tissue is within several centimeters of the surface of the body.

A point-of-care device based upon the generation of coherent laser light, that could be used to screen patients for breast cancer where the suspected malignant tumor is located either on the surface or deep within tissue, and for other similarly located malignances, and which can also assess the effects of therapy, would be an important addition to the armamentarium for breast cancer and similar diseases. Based upon light, such a device would not present the health risks associated with repeated application of X-rays as does mammography.

Deep Optical Scanning (DEOS) is similar to DOS in that it employs coherent, laser generated, light and presents no health risks. However, because it performs deep optical scanning, DEOS enables detection of cancerous tumors far below the surface and tracking of their response to applied therapies. DOS cannot do this. DEOS is based upon the technical area usually referred to as Nonlinear Optics (NLO). Nonlinear Optics is the branch of optics that describes the behavior of light in nonlinear media—often referred to as "NLO material." This is transmission media in which the dielectric polarization, P, responds nonlinearly to the electric field, E, of light. It is established that biological systems, including the human body and specifically the breast, are in fact NLO material. Accordingly, techniques that are associated with NLO can be used for the detection of subsurface malignant tumors—such as those in the breast and analogous cancers. Following detection and diagnosis, these techniques can also be used to determine the response of the malignancies to the application of therapies.

There are several NLO techniques. DEOS involves one of these techniques: Second Harmonic Generation (SHG). SHG is especially attractive because it leads to simple implementation of DEOS. With DEOS the breast is irradiated with coherent laser light at different wavelengths. Most of this light is reflected from the surface of the breast. However, a certain quantity of light penetrates deeply into the breast and interacts with the underlying tissue in a nonlinear manner. Specifically, incident light of a given wavelength will interact with the sub-surface tissue, generating scattered light at half the wavelength (i.e., double the frequency, or the second harmonic). This scattered light comes out of the breast where it is separated from the incoming incident light by appropriate wavelength filtering to form an optical signal that can be electrically converted for analysis.

At present, there are a number of justifiable concerns regarding clinical application of DEOS:

First, there is a need to make the device or system small enough to be portable so that it can be conveniently located and employed in a physician's office or a CCC, rather than at a centralized laboratory. The system should be easily transportable from one examining room to another. With such portability, the physician will be able to shorten the cancer detection process, and if cancer detected by the system is subsequently confirmed through a conventional biopsy, quickly determine if a program of therapy is successful. This allows for greater efficiency in physician-patient interaction. It also has a much more positive impact on the experience for the patient in this stressful situation.

Second, the measured SHG information should be processed to give the physician a transparent and understandable determination of the detection of cancer or the response to therapy. Presenting the raw SHG information directly to the physician is not worthwhile. A physician in clinical practice is always worried about time constraints and has little patience for deciphering information. Presentation should therefore be simply stated. However, the measured SHG information behind such presentation should be properly archived and accessible for the physician. This will allow the physician to examine the measurements underlying a reported detection and the response to therapy.

The invention presented below builds on the DEOS approach and addresses all of these concerns.

SUMMARY OF THE INVENTION

Example embodiments of the present invention use DEOS to implement a point-of-care device or system for detection of malignant tumors located on the surface or deep within tissue, and for assessment of the effects of therapy. In order to simplify the discussion of the present invention, only its application to breast cancer will be considered. The application to other cancers is straightforward.

Example embodiments of the present invention involve using SHG and forming an Energy Spectral Density (ESD) corresponding to the many incident wavelengths of the resulting scattered optical signals. However, with appropriate modifications the present invention can be used with other NLO processing techniques besides SHG. By way of example, other NLO techniques might include Raman amplification, Brillouin scattering, Difference Frequency Generation and Third Harmonic Generation. Any of these additional NLO techniques may be used for tissue characterization and cancer detection. The ESD is a digitized version of the SHG energy spectrum and an important aspect of the present invention. The scattered light as a result of SHG is very low in amplitude/intensity. The ESD is calculated as an integral of the power of the scattered signals over a sufficiently long period of time. This results in measurements that are sufficiently large to permit discrimination between benign/non-cancerous tissue and malignant/cancerous tissue.

Example embodiments perform automated discrimination in a non-invasive manner by using a combination of digital signal processing (DSP), approximation and smoothing techniques, and artificial intelligence (AI), to determine whether the tissue being presented is either normal or has a malignancy.

As mentioned above, the spectrum of the scattered light will be different depending upon whether the incident coherent laser light interacts with normal tissue or with a malignancy buried within the tissue. This is essentially due to differences in chemical and structural properties of normal tissue and a malignancy, which differences present themselves as different optical properties such as reflection coefficient and refraction coefficient. It has been established that SHG can be used in microscopy to produce images in which normal tissue is visually distinguishable from malignant tissue. By way of example, FIG. 1 shows a graph 11 of the differences between the intensities of images derived from SHG microscopy for normal and malignant breast tissue. The images are not shown, but it is possible to analyze the images through visual inspection. However, it is more amenable to signal processing and automated discrimination if the images are converted to mathematical representations, including corresponding ESDs.

Example embodiments apply an ESD as input to an AI subsystem. The AI subsystem outputs an indication of whether the ESD corresponds to either normal tissue or a malignant tumor, and with what level of confidence. By way of example, the output of the AI subsystem follows the Breast Imaging Reporting and Data System (BI-RADS) established by the American College of Radiology. The BI-RADS assessment categories are: $B_0$—"incomplete," $B_1$—"negative," $B_2$—"benign findings," $B_3$—"probably benign," $B_4$—"suspicious abnormality," $B_5$—"highly suspicious of malignancy" and $B_6$—"known biopsy with proven malignancy." However, other classifications indicating the presence or absence of cancer may be used. In one embodiment, the AI subsystem is adapted to fewer categories, for example only the two categories "Benign" and "Malignant." By presenting a physician or other user with categories and confidence levels, the AI subsystem provides an easy to understand alternative to raw SHG or ESD information.

The AI subsystem is designed so that it has a high sensitivity and specificity. The sensitivity and specificity indicate a degree of trust in the output. Sensitivity can be represented by the percentage of decisions indicating a malignant tumor is present when, in fact, it actually is present. This is similar to the "probability of detection" concept in radar systems. Specificity can be represented by the percentage of decisions which indicate a malignant tumor is present when, in fact, it is not present. This is similar to the "probability of a false alarm" concept in radar systems. The AI subsystem may also calibrate itself to results of a conventional biopsy, using biopsy results as a reference standard for determination of the presence or absence of a malignant tumor.

If a malignancy is detected by the AI subsystem, the detection can be confirmed by tissue diagnosis with an actual biopsy, and a program of therapy is commenced. DEOS can then be reapplied to determine quickly if the therapy is working, by monitoring the patient's progress through repeated measurements of ESD over time, e.g., intervals of weeks or months. If a patient is responding to therapy, it is expected that the ESD corresponding to the cancerous lesion should be "moving" so as to come closer to, and ideally coincide with, the ESD corresponding to normal tissue. The AI subsystem may identify such movement when presented with the patient's ESD history as an input.

An AI subsystem may include a neural network that produces an initial decision and an expert system that refines the initial decision by executing a rule based logical reasoning algorithm to determine, based on at least one data source, whether the initial decision should be changed. The expert system outputs a final decision including a qualitative indication of whether cancer is present—a BI-RADS classification is one example. The final decision may also include a confidence level for the decision expressed, for example, as a percentage.

Data sources may include external databases containing imaging data for other patients, statistical analyses of imaging data for other patients, medical literature, and other sources of cancer-relevant medical data. Such databases may be configured to provide an opinion, in automatic response to a query from the AI subsystem, as to whether medical data collected for the patient of interest (including, but not limited to ESD data) indicate the presence of cancer. The opinions may, for example, be based on a comparison to or derived from corresponding medical data stored in the databases. Data sources may also include responses from human experts who manually evaluate the medical data collected for the patient of interest.

Example embodiments of expert systems execute various algorithms for refining an initial decision using rule based logical reasoning, which may involve sequential and/or parallel operations on different sets of cancer-relevant medical data for the patient of interest and possibly the patient's family.

Example embodiments include a detection system with opto-electronic elements and computational elements configured for portability. Such elements include, for example, avalanche photo diodes that efficiently convert reflected optical signals into electrical signals for processing, miniature optical arrangements for switching between laser transmissions of different wavelengths and scanning laser beams over a target area, and multiplexing techniques that enable sharing of an optical transmission medium such as a single fiber optic cable.

DETAILED DESCRIPTION

Figure 1:
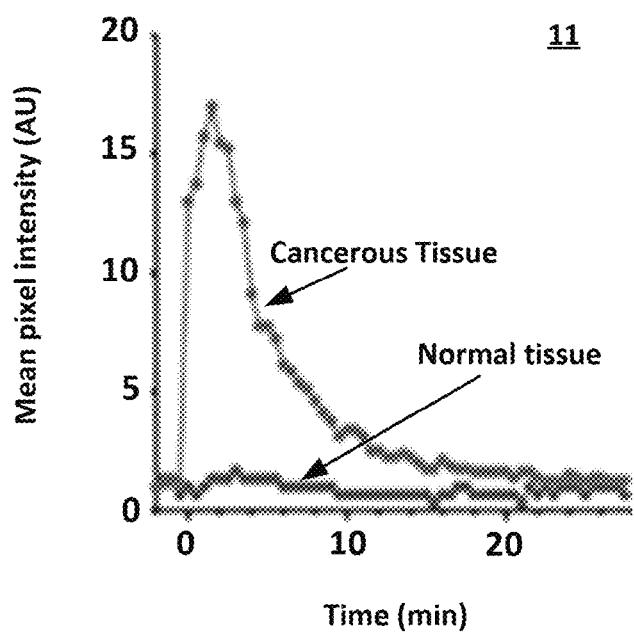
FIG. 1 is a graph illustrating differences in intensity levels of images derived from SHG microscopy for normal and malignant breast tissue.
Figure 2:
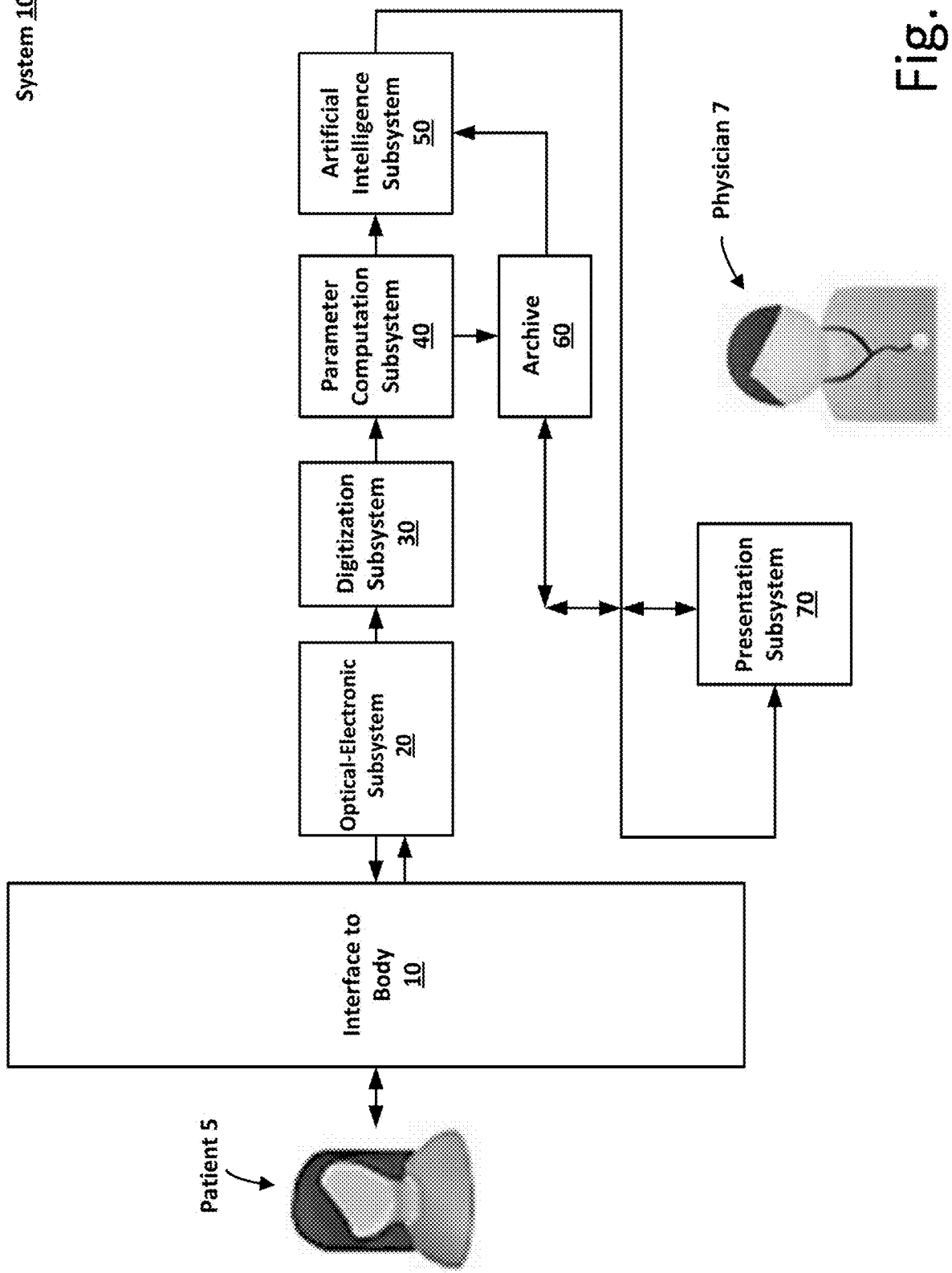
FIG. 2 is a block diagram of a system for cancer detection according to an example embodiment of the present invention.

FIG. 2 is a block diagram of a system 100 for cancer detection according to an example embodiment of the present invention. The system 100 may be implemented as a single, portable device. Alternatively, the system 100 may be implemented as a plurality of separate components that may be in wired or wireless communication with each other. The system 100 may include an Interface 10 to the body of a patient 5, an Optical-Electronic Subsystem 20, a Digitization Subsystem 30, a Parameter Computation Subsystem 40, an Artificial Intelligence Subsystem 50, an Archive 60, and a Presentation Subsystem 70. Each of these subsystems will be described separately and may be operated by a physician 7. However, it will be understood that subsystems can be combined into a single hardware and/or software arrangement. Some components may be remotely located, for example, components that carry out processing over the Internet via Cloud computing.

Figure 3:
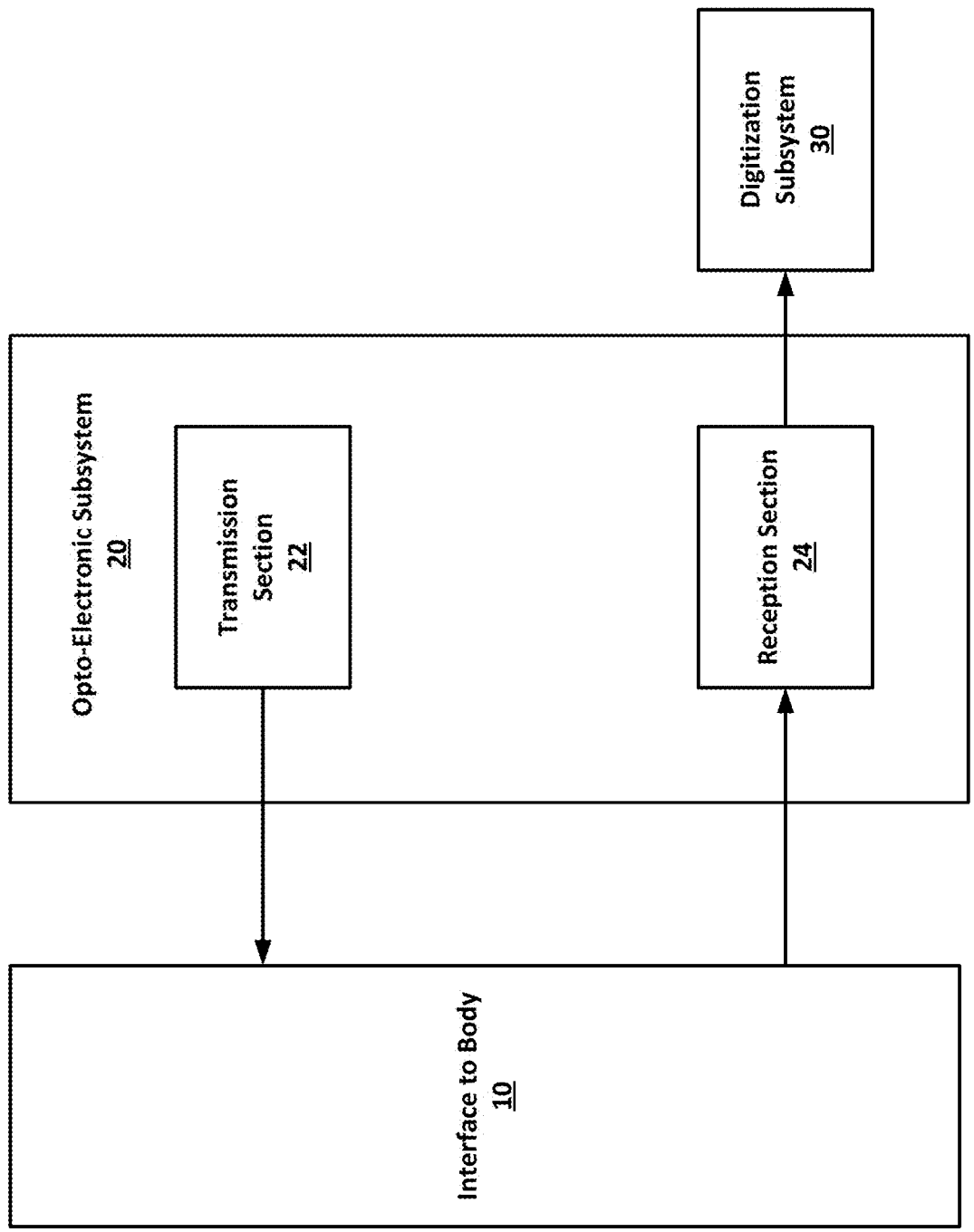
FIG. 3 is a block diagram of an opto-electronic subsystem according to an example embodiment of the present invention.

FIG. 3 is a block diagram showing the overall structure of the Opto-Electronic Subsystem 20, which includes a Transmission Section 22 and a Reception Section 24. FIG. 3 also shows the communicative coupling of the Opto-Electronic Subsystem 20 to the Interface 10 and the Digitization Subsystem 30.

Transmission Section of the Opto-Electronic Subsystem

Figure 4:
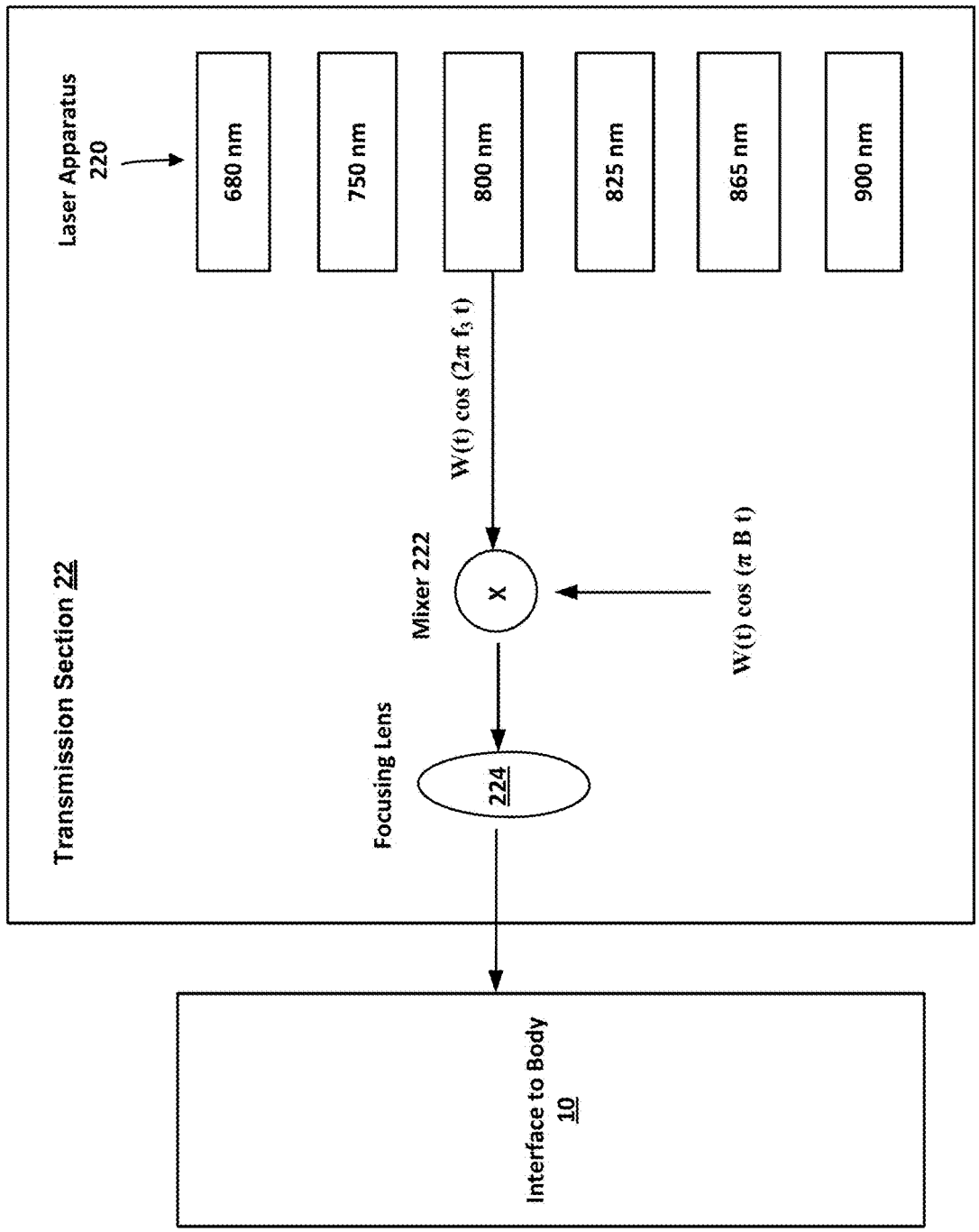
FIG. 4 is a block diagram of a transmission section of an opto-electronic subsystem according to an example embodiment of the present invention.

FIG. 4 shows an example embodiment of the Transmission Section 22, which includes circuitry generating the coherent light that illuminates the patient's breast. The circuitry generates the coherent light for each laser in the laser apparatus (or a single laser at different tuned wavelengths) over a specific time interval of "T" seconds. The coherent light from each laser is amplitude modulated over a bandwidth "B" Hz or equivalently a wavelength range of "$\Delta\lambda$." By way of example, "B" could be 250 MHz. The value of B is generally driven by constraints on the electronics used to implement the system. The light is then supplied to an optical apparatus including a focusing lens.

The circuitry includes a laser apparatus comprising either a single diode laser which is tunable to "N" different wavelengths over the wavelength range $[\lambda_L, \lambda_U]$ or a plurality of different diode lasers each tuned to a different wavelength in the range $[\lambda_L, \lambda_U]$. This corresponds to the frequency range $[f_L, f_U]$. N is any integer greater than or equal to one. The different wavelengths are $\lambda_1, \lambda_2, \ldots, \lambda_N$. These wavelengths can be thought of as equivalently corresponding to center frequencies $f_1, f_2, \ldots, f_N$. The range $[\lambda_L, \lambda_U]$ would typically extend from $\lambda_L$=650 nm to $\lambda_U$=1350 nm. Wavelengths outside of this range are also possible. However, this particular range defines a near-infrared window (also called the therapeutic window) where light has a maximum depth of penetration into tissue. By way of example, and as shown in FIG. 4, if N=6 the wavelengths associated with six corresponding diode lasers could be $\lambda_1$=680 nm, $\lambda_2$=750 nm, $\lambda_3$=800 nm, $\lambda_4$=825 nm, $\lambda_5$=865 nm, and $\lambda_6$=900 nm. For simplicity, the single laser alternative is not shown in the drawings.

The Transmission Section 22 includes a laser apparatus 220 formed by a bank of diode lasers. Diode lasers efficiently generate coherent light in the near infrared spectrum of interest. Each of these lasers transmits in sequence for a duration equal to T. That is, a first laser transmits for T duration, then a second laser transmits for T duration, and this continues until the last laser has completed its transmission. T can be considered to be quite long, possibly on the order of seconds. However, this is not an issue because real time processing is not required for the system to be successfully applied. The sequencing of the transmissions from the lasers is accomplished by a switching arrangement which is not shown.

FIG. 4 shows a single transmission from the third (800 nm) laser. This transmission is representative of a transmission from any of the lasers in the laser apparatus 220. The transmission is characterized as a cosine function multiplied by a window function "W(t)." The window function is a periodic square wave multiplied by a pseudo random sequence of 0's and 1's, and has a period of "Tw" seconds, where Tw<<T. For example, Tw may be on the order of microseconds. The transmission is mixed by a mixer 222 with the same windowing function multiplied by cos (πBt). The modulating pseudo random sequence has the effect of "whitening" the power within the B Hz modulating bandwidth, making it flat. The inputs to the mixer 222 are synchronized with respect to W(t). The mixing produces an amplitude modulated optical waveform centered around the frequency $f_3$ (for the third laser) and having a bandwidth of "B" Hz. B typically would be several hundred MHz, for example 250 MHz. The output of the mixer 222 can be represented by the formula W(t) {cos $(2\pi(f_3-(B/2))t)$+cos $(2\pi(f_3+(B/2))t)$}. The amplitude modulated optical signal is then beamed to at least one focusing lens 224 which transmits the optical signal to the Interface 10. Although FIG. 4 only shows one lens, the lens 224 can be augmented with multiple lenses and mirrors in order to better illuminate the breast.

Interface to the Body

Figure 5:
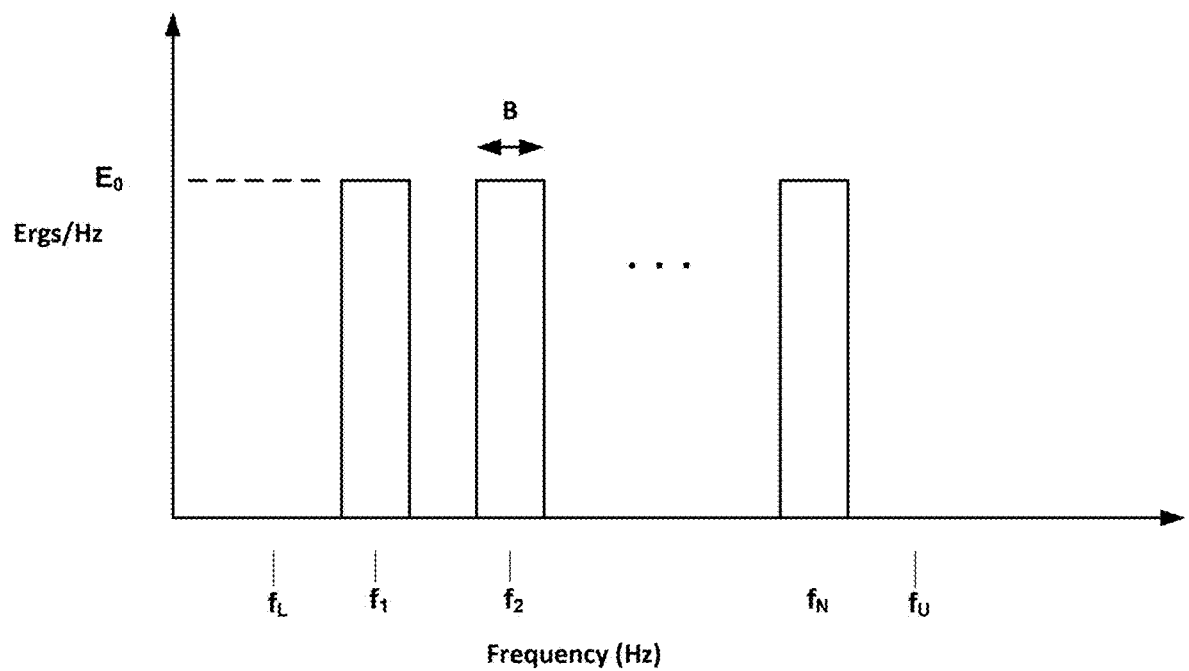
FIG. 5 is a graph of incident ESDs according to an example embodiment of the present invention.

The Interface 10 may be a wearable or otherwise unobtrusive appliance placed over all of part of the surface of the patient's breast without causing discomfort. Because in certain circumstances only part of the breast is covered, repeated applications of the system, e.g., to different breast locations, may be required. The area of the body so covered will be referred to herein as the "active area." The Interface 10 may include an arrangement that conveys coherent light of different wavelengths, λ to the active area. The arrangement applies the light received from the Transmission Section 22 so that the light illuminates (essentially radiates) and penetrates the breast. Importantly, the power from each of the lasers is constrained to a level where the radiating light does not cause harm to the target tissue. The radiating light from any of the lasers can be characterized by its ESD. This is illustrated in FIG. 5, which shows an example graph in the frequency domain of the ESD, in units of Ergs/Hz, for incident light from a plurality of lasers. In the example of FIG. 5, the ESDs all have the same value, $E_0$.

The radiating light is meant to penetrate and probe the underlying tissue. With DOS, the tissue region that is of concern (referred to herein as the Region of Interest or ROI) is self-evident; because the ROI lies on the surface of the patient's body, it is obvious where the incident laser light needs to directed. However, with DEOS the ROI is below the surface. Therefore, the ROI may be obtained through an acquisition process in which the laser beams scan over a region on the breast that overlies the ROI. The scanning may break the region up into individual cells, each defined by coordinates of an appropriate reference system, e.g., spherical coordinates, (φ, θ)-elevation and azimuth. The resulting reflections from each cell are then processed. The acquisition process can be carried out by one of three approaches, Stepped Raster Scanning (SRS), Digital Light Processing (DLP), and Stepped Optical Phased Array (SOPA).

With SRS, the laser beam sweeps horizontally across the breast, e.g., from left to right in a straight line, then turns back and sweeps the next line at a certain distance below the previous line. During each horizontal sweep the motion is not continuous. Rather, the beam dwells at each cell for a certain period of time, $T_{dwell}$, illuminating the cell with light and allowing the reflections to be collected. The discrete steps in the horizontal sweep are in contrast to the way scanning is done in conventional analog television. During the horizontal sweep the vertical position is also steadily moving downward but also by a discrete stepping motion. In other words, during the horizontal sweep there is stepping both horizontally and vertically, so that each scan line slopes downwards. Successive horizontal sweep lines are carried out for a programmed period in order to cover the entire area of the breast which may be of concern, e.g., the entire active area.

With DLP, microscopic mirrors are arranged in a matrix on a semiconductor chip usually referred to as a Digital Mirror Device (DMD). Each of these mirrors is used to reflect the incident laser light to a different cellular region of the breast. These mirrors can be toggled so that the illumination of the cells is done sequentially and corresponding receptions processed sequentially. However, it may also be possible to have these mirrors act in parallel with mirrors at the corresponding receivers.

With SOPA, a phase profile is imposed on each laser beam. By varying the phase profile, the laser beam can be steered through different angles. Specifically, the phase of the laser beam can be controlled using adjustable surface elements. The optical properties of the surface elements on a microscopic scale are dynamically controlled. Similar to SRS, SOPA involves steering of the beam to a given cell, where the beam dwells for a period of time. After the reflection is collected, another cell is illuminated by stepping in a specific direction. An array of optical phase shifters is used to effect this dynamic motion. The array of optical phase shifters is usually realized through lithographic patterns driven by an electrical network or by liquid crystal techniques.

Reception Section of the Opto-Electronic Subsystem

Figure 6:
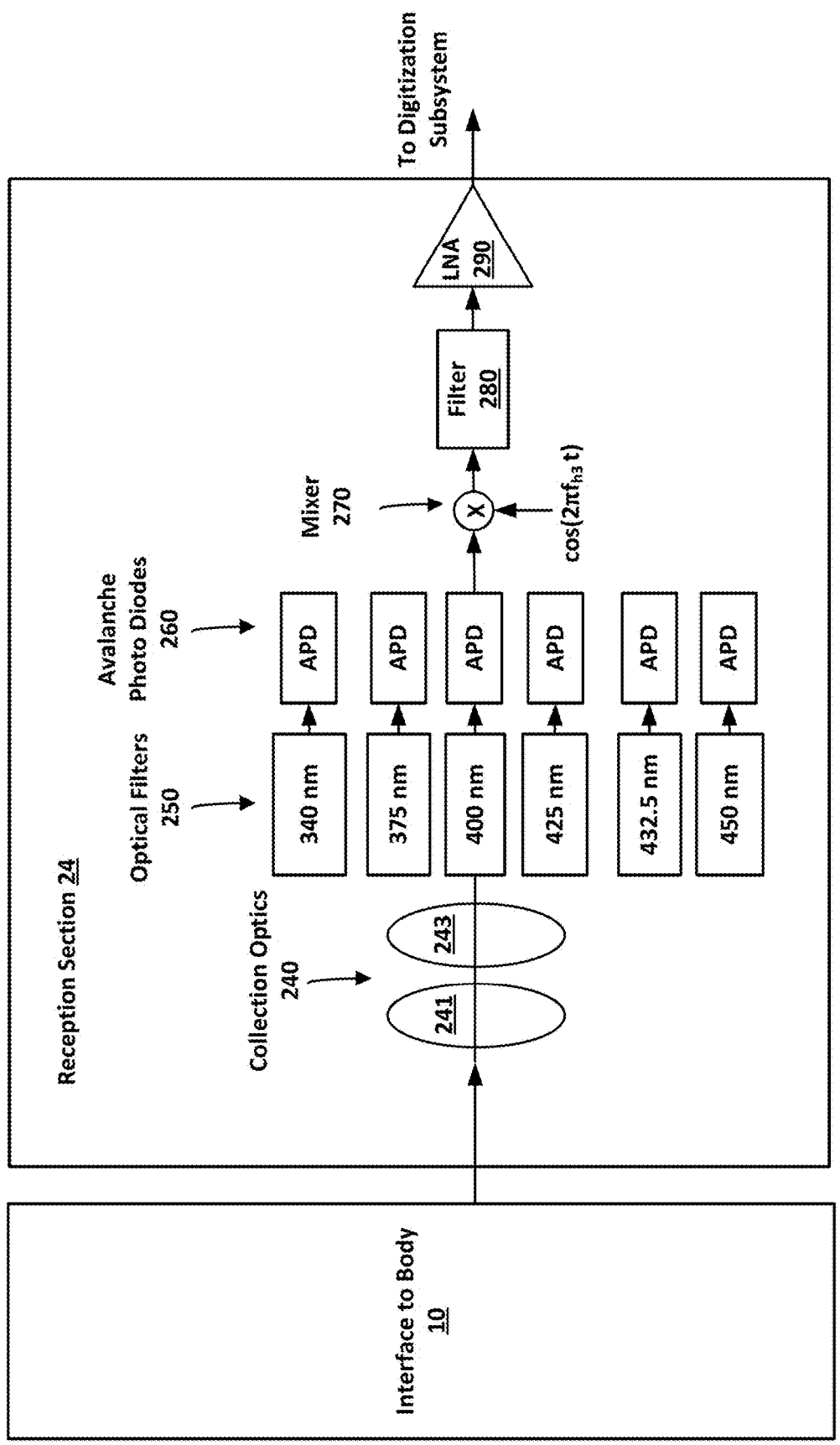
FIG. 6 is a block diagram of a reception section of an opto-electronic subsystem according to an example embodiment of the present invention.

FIG. 6 shows an example embodiment of the Reception Section 24. For illustration purposes, the example discussed in connection with the Transmission Section of FIG. 4 is continued. However, the number of filters, the tuning wavelength of each, the modulation bandwidth and other parameters may change for specific designs.

The Reception Section 24 includes components that communicate with the Interface 10 to receive reflected light. Beginning on the left hand side of FIG. 6, the Interface 10 receives and outputs to the Reception Section 24 a combination of reflections produced in response to the incident coherent laser light. The reflections include reflections from the surface of body (essentially DOS reflections) and outwardly radiated SHG reflections from below the surface of the body. For example, the reflections may include a combination of light scattered from the internal tissue and/or malignancy, and light scattered from the surface or near the surface of the breast.

The reflected light is first supplied to Collection Optics 240, which include at least one lens (241, 243) for focusing of the received light. The Collection Optics 240 concentrate the reflected light onto an area at which it can be appropriately processed by the rest of the Reception Section. In addition to the at least one lens, the Collection Optics may include mirrors.

The lenses 241, 243 are followed by a bank of optical filters 250. The filters take the focused light and separate the SHG reflections from the surface reflections. Each optical filter is tuned to the wavelength of a different second harmonic generated. In other words, there are N filters and they are tuned respectively to $\lambda_1/2, \lambda_2/2 \ldots \lambda_N/2$, for example, 340, 375, 400, 425, 432.5 and 450 nm. The second harmonic generated for each incident laser light will be centered at twice the corresponding center frequency-equivalently at half the wavelength of the incident light. The sequence of transmissions of the incident coherent light from the different lasers is known. Consequently, during a given time interval the output of the corresponding optical filter can be dealt with for further processing.

The light coming out of each of the N filters is supplied to a corresponding Avalanche Photo Diode (APD) in a bank of APDs 260. Alternatively, it is possible to use a single APD covering the entire wavelength range shown. For simplicity, FIG. 6 only shows the output of the APD corresponding to the third diode laser of FIG. 4 and the 400 nm optical filter. Each APD converts the filtered light it receives into an electrical format, e.g., a time varying voltage.

A mixer 270 brings the electrical signal from each APD to an Intermediate Frequency (IF) band, e.g., by mixing with a signal represented by the function $\cos(2\pi f_{h3} t)$. The frequency of the mixing signal of course depends upon the center frequency of the output of the APD, and is labeled "$fh_3$" to denote that the mixing signal corresponds to the third diode laser in FIG. 4. The electrical signal becomes demodulated as a result of the mixing, and is provided to a filter 280 that eliminates high frequency components so that only the "image" of the voltage output of the APD around the IF remains. It is the energy in this particular signal which, with proper scaling, can represent the energy of the SHG in the frequency band of the third diode laser. The bandwidth of this particular frequency is centered around the IF and is B Hz wide.

The output of filter 280 is provided to a Low Noise Amplifier (LNA) 290 to bring it up to a level appropriate for further processing by the Digitization Subsystem 30. It is important to note here that the power received from a typical SHG reflection is usually too low to permit easy detection. Therefore, the amplification provided by the LNA 280 facilitates detection when combined with the ESD calculation described below.

Digitization Subsystem and ESD Calculation

Figure 7:
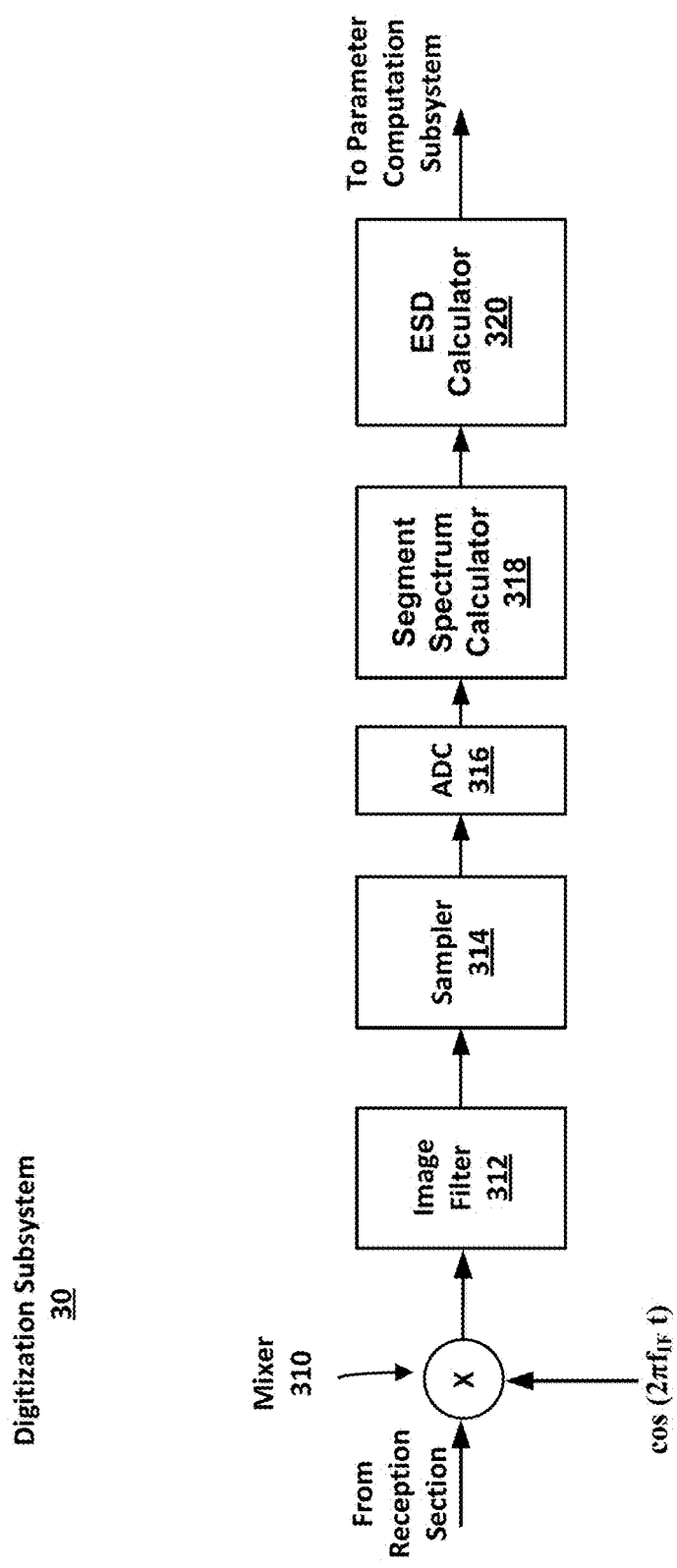
FIG. 7 is a block diagram of a digitization subsystem according to an example embodiment of the present invention.

The Digitization Subsystem 30 is shown in FIG. 7. The voltage input to the Digitization Subsystem 30 is centered at an IF frequency, "$f_{IF}$" and should be brought to a base band level in order to permit digital processing. This is accomplished by a mixer 310 that mixes the voltage input with a signal represented by the function $\cos(2\pi f_{IF} t)$.

Following mixing, an Image Filter 312 removes the high frequency "relic"(also referred to as the "image" in the terminology of superheterodyne receivers). The result is an analog base band signal which has a double sided bandwidth of B Hz, and which represents the SHG resulting from the light produced by the third diode laser.

A Sampler 314 samples the output of the Image Filter 312 at a rate above the Nyquist frequency, i.e., a rate greater than B samples per second. For the example being considered this is several hundred Mega Samples Per Second (MSPS).

The sampled output is supplied to an Analog to Digital Converter (ADC) 316 with sufficient dynamic range to accommodate the sample stream. Additionally, the ADC 316 operates at a high number of bits per sample and a high Equivalent Number Of Bits (ENOB) per sample. ENOB is a performance metric which takes non-linearity in the digitization processing into account. The accuracy level of the ADC affects the ultimate reliability of the detection of cancerous tissue. Strictly by way of example, a value of 16 bits per sample with an ENOB of 11 would provide sufficient accuracy. The ADC 316 produces a resulting stream of digitized samples corresponding to the original T second transmission.

The output of the ADC is provided to a Segment Spectrum Calculator 318 that considers successive sequences of samples of duration "$T_B$," where $T_B$ is a sufficiently long multiple of $B^{-1}$ but is much less than T, and where T is on the order of seconds. For each $T_B$ length sequence, the Segment Spectrum Calculator 318 computes the equivalent amplitude of the base band voltage spectrum which will be referred to herein as $|V(f)|$. For each grouping of "K" such spectrums (where K is a sufficiently large integer, e.g., on the order of 100), the Segment Spectrum Calculator 318 computes a corresponding "Segment ESD" by first squaring each $|V(f)|$ to obtain $|V(f)|^2$, and then taking an arithmetic average of the K spectrums. For the entire T second transmission there will be a total of $T/KT_B$ Segment ESDs computed and supplied to an ESD Calculator 320.

The ESD Calculator 320 sums the Segment ESDs, thereby computing the time integral of the power spectral density over the entire T second transmission. This sum represents an accurate estimate of the ESD corresponding to the SHG from a single laser, e.g., the third diode laser of FIG. 4. The ESD Calculator 320 may perform corresponding computations for each of the remaining laser transmissions. This processing step is important as it effectively takes the individual $|V(f)|$'s, which are quite low for SHG (with after amplification by an LNA), and represents them by a much larger value that is appropriate for processing and ultimate discrimination of tissue with benign tumors from tissue with malignant tumors. A composite of all ESDs computed in this manner (corresponding to SHGs from the N laser transmissions) can be denoted by the set of functions $\{E_i(f)$ where $i=1, \ldots, N\}$. The totality of this function set is denoted by EF(f). For illustration purposes, and without loss of generality, a frequency domain characterization is mostly employed in the present disclosure. However, equivalent wavelength domains characterizations exist. For example, EF(f) can be equivalently characterized in the wavelength domain as $\{E^+_i(\lambda)$ where $i=1, \ldots, N\}$.

Figure 8:
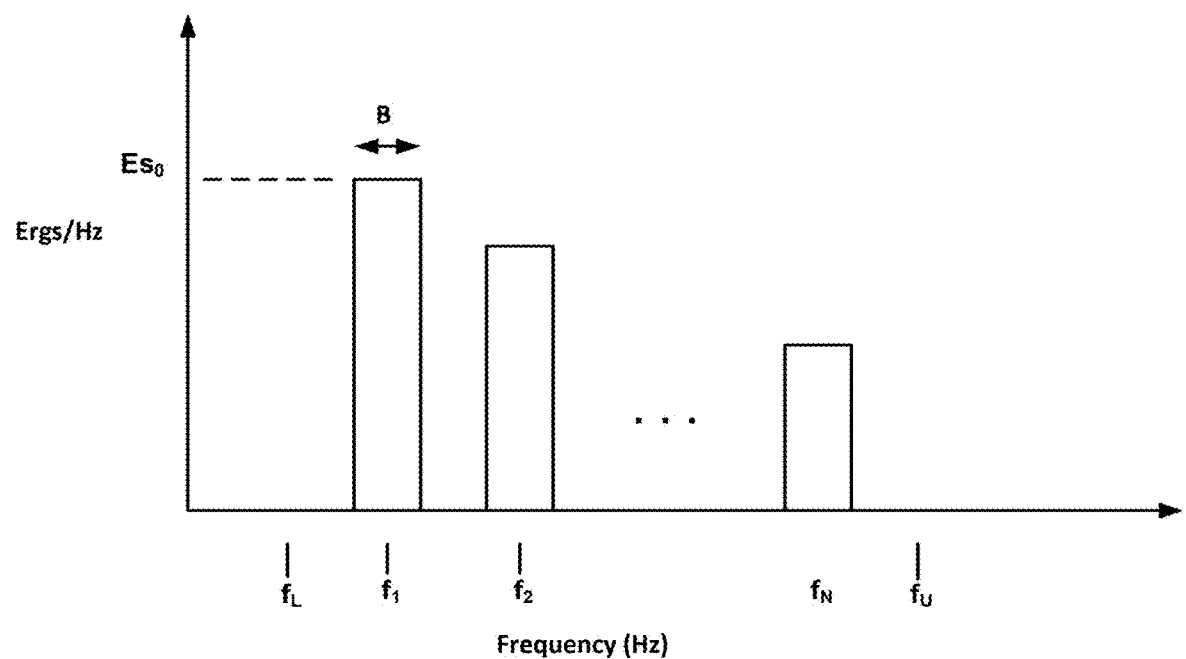
FIG. 8 is a graph of reflected ESDs according to an example embodiment of the present invention.

EF(f) corresponds to an initial estimate of the composite ESD of all SHGs and is provided to the Parameter Computation Subsystem 40. This initial estimate has gaps due to the light generated by the laser at each of the tuned wavelengths being limited to the bandwidth B. FIG. 8 shows an example EF(f) function. In FIG. 8, the ESD of the SHGs is much less than the incident light shown in FIG. 5, thus $E_{SO} \ll E_0$.

There is significant importance in using the ESD as a primary parameter to be processed rather than the spectral amplitude $|A(f)|$. As mentioned previously, the light intensity collected from the scattered SHGs can be quite low. Using the ESD, where it is collected over a T second period, allows the aggregation of low amplitudes into a larger energy signal. T can be chosen appropriately to achieve this. Although large T values will slow down processing, the computation of the ESDs is still essentially real-time and presents no problem for the application of cancer detection.

Parameter Computation Subsystem and Archive

Figure 9:
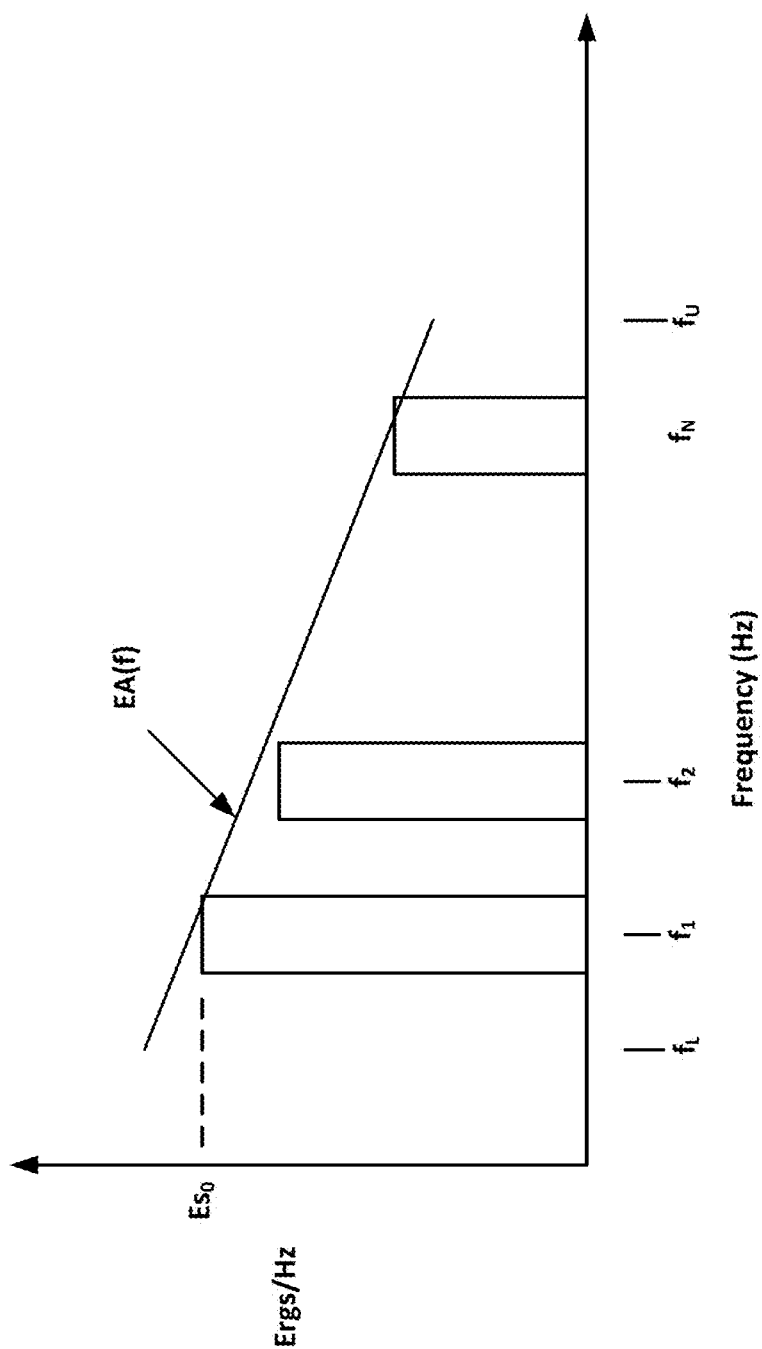
FIG. 9 shows an approximation of the ESDs in FIG. 8.

The Parameter Computation Subsystem 40 fills in the gaps in the function EF(f) by applying approximation and smoothing algorithms to derive a function EA(f) as a continuous function from $f_L$ to $f_U$. This approximation function is illustrated in FIG. 9. It is important to fill the gaps before discrimination, e.g., prior to input to the Artificial Intelligence Subsystem 50. Alternatively, gap filling performed within the Artificial Intelligence Subsystem itself, prior to discrimination processing, could lead to greater efficiencies in the use of computational resources.

With respect to the human body, as represented by the breast, the functional relationship between scattered incident radiation and frequency (or wavelength) should be continuous and mathematically differentiable in order to provide for discrimination between scattered radiation from normal tissue and from a cancerous tumor. This puts constraints on the function. Continuity in the inputs and the derivatives of the inputs presented to the Artificial Intelligence Subsystem 50 are expected. Such continuity provides useful information. Filling in the gaps creates this continuity and may allow the pattern classification and decision processes of the Artificial Intelligence Subsystem 50 to operate more efficiently and with greater reliability, to provide greater sensitivity and specificity in the ultimate BI-RADS outputs. Several gap filling methods are described below. Each method is described individually. However, the Parameter Computation Subsystem 40 may use any of the methods, either individually or in a combination on two or more, for smoothing and filling in the gaps.

One way to fill gaps is to consider EF(f) at a group of "J" sample frequencies; $f_{P1}, f_{P2}, \ldots, f_{PJ}$—specifically $EF(f_{P1})$, $EF(f_{P2}) \ldots EF(f_{PJ})$, and then apply a polynomial approximation in which a polynomial function is fitted to the group. A polynomial of a specific and high enough degree, "m," can be determined which will approximate the J samples to within an acceptable degree of error. The degree of error will decrease as m increases. The type of polynomial may be chosen so as to minimize a particular measure of error. For example, Chebyshev polynomials may be used to minimize the maximum error. Lagrange Interpolation polynomials are another type that may be suitable for use in approximation.

A second way to fill gaps uses spline functions for the approximating polynomial. The spline functions are piecewise polynomials of degree m that are connected together at points known as "knots." These have "m−1" continuous derivatives. The piecewise nature allows better approximation when the physical parameters vary significantly from region to region. This may well be the case for the physical parameters which give rise to the EF(f) function.

There are other gap filling methods that the Parameter Computation Subsystem 40 can use which do not involve polynomial approximation. A third method is based upon the fact that the optical parameter, the composite ESD over the entire frequency (or wavelength) domain is well behaved, continuous and with continuous derivatives everywhere. Therefore the composite ESD can be considered analytic and the technique of analytic continuation can be applied. Analytic continuation is a mathematical technique that exploits a property of complex functions where if the value of the function is known on a finite set of points, then the value can be determined everywhere. In the case of the EF(f) function, the value of the function is known where there are no gaps and as a result, the function can be extended through the gaps. This is usually done by employing infinite series to calculate the function.

A fourth method is based upon the Whittaker-Shannon interpolation formula, also known as sinc interpolation. This method is generally used to construct a continuous-time band-limited function from a sequence of real numbers. It can be applied here as well.

After applying any of the above described gap filling methods, the gaps in the approximations of EF(f) will have been filled in. As mentioned earlier, this resulting function is denoted EA(f) and is supplied to the Artificial Intelligence Subsystem 50. Specifically, "M" samples are taken of EA(f) at M frequencies and then passed to the Artificial Intelligence Subsystem. Here M is an integer≥N. The M frequencies are denoted as $f_{A1}, f_{A2}, \ldots, f_{AM}$. The corresponding M samples of EA(f) are denoted as $E_1, E_2, \ldots, E_M$. The samples may be taken equally spaced over the entire frequency band from $f_L$ to $f_U$ or they may be unequally spaced.

The Parameter Computation Subsystem 40 also outputs EA(f) to the Archive 60 for storage. The Archive 60 stores EA(f) samples for possible future examination along with labels identifying the patient and date on which the measurement was obtained.

Artificial Intelligence Subsystem

Figure 10:
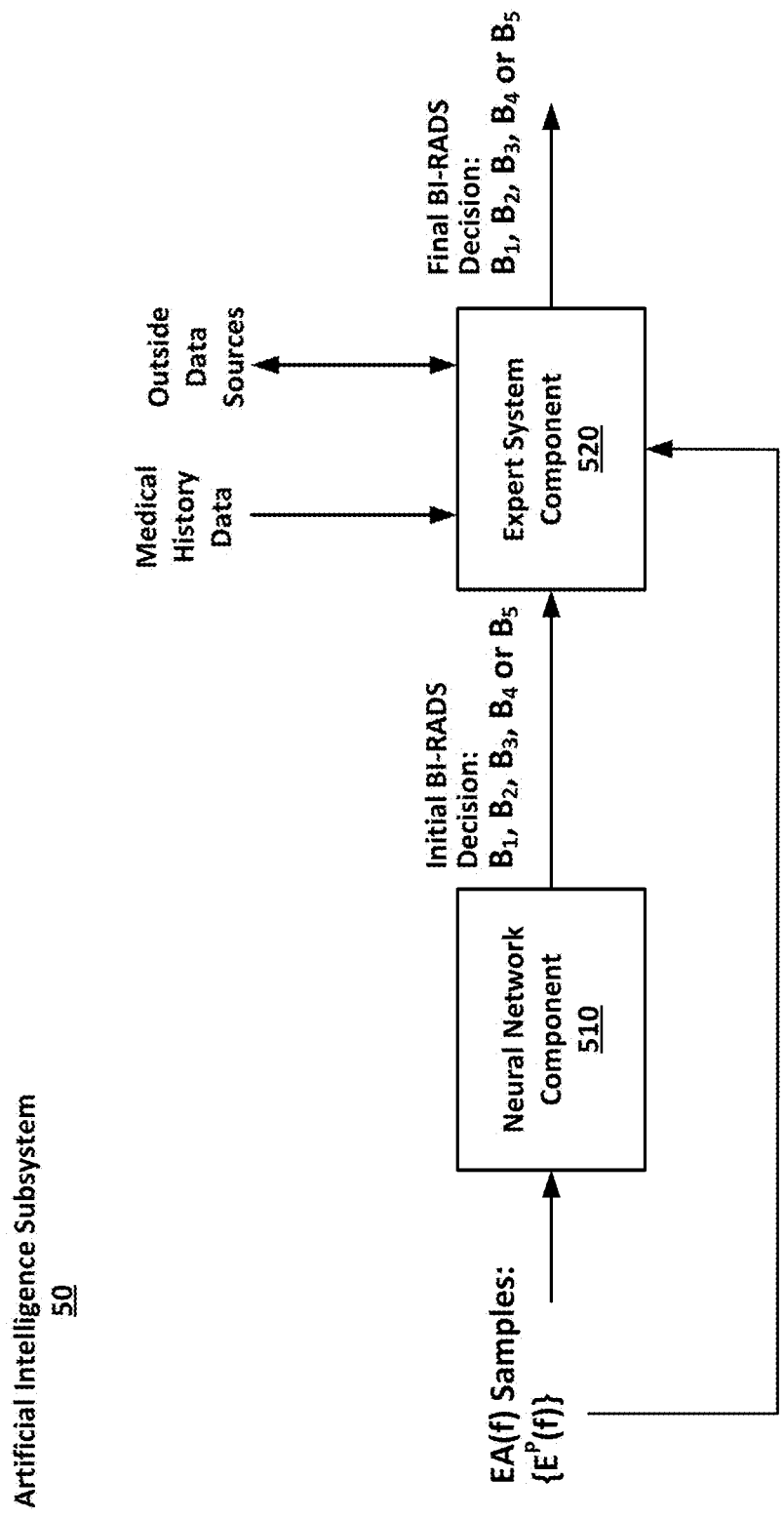
FIG. 10 is a block diagram of an artificial intelligence subsystem according to an example embodiment of the present invention.

FIG. 10 shows an example embodiment of the Artificial Intelligence Subsystem 50, which can be implemented with a hybrid architecture including a Neural Network component 510 and an Expert System component 520.

A neural network is a computing device configured to look for and classify patterns of data. As a computing device, it has inputs and produces outputs. However, it is not programmed in the conventional sense. Rather, it is trained. Once trained it can be actively applied. In training it is given many examples of inputs and corresponding outputs. The training adapts the neural network's internal structure so that when it is provided with a non-example input it will produce a meaningful corresponding output. When training, the inputs are usually referred to as "features." The resulting internal structure is designed to mimic the interconnection of neurons in the human brain attempting to recognize patterns in the same inputs. There are many structures and topologies of neural networks. However, for purposes of the discussion here, the general structure shown in FIG. 11 will be used.

Figure 11:
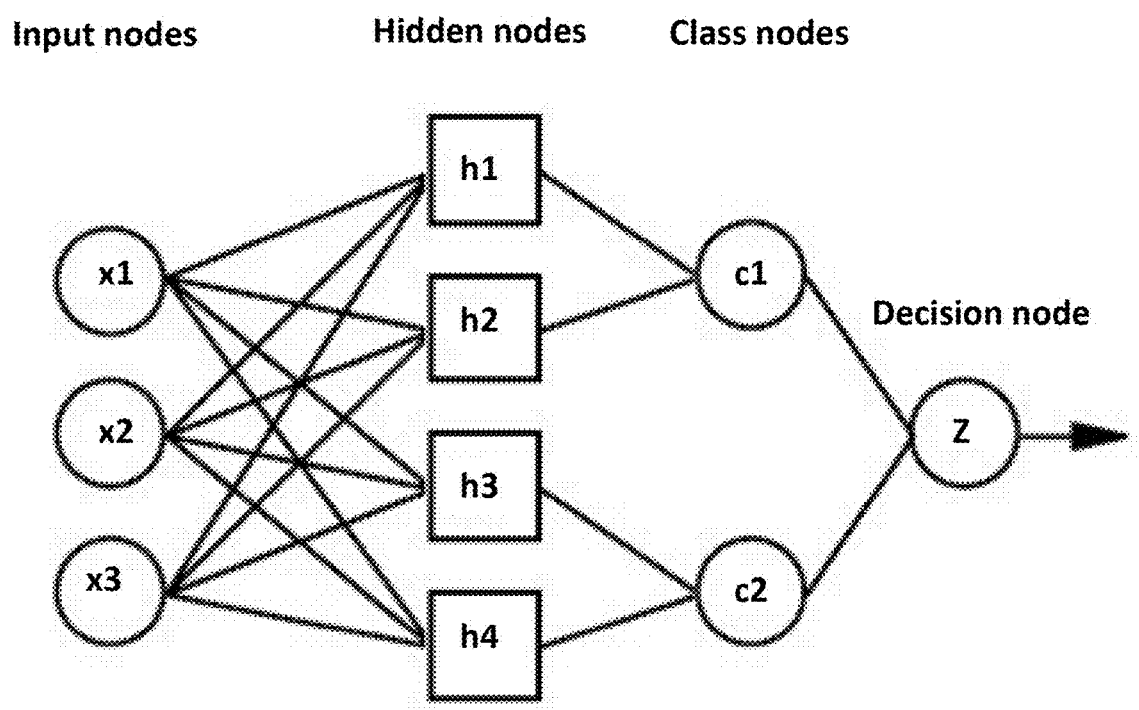
FIG. 11 shows an example neural network.

FIG. 11 shows an example neural network that accepts input at Input Nodes, x1-x3 and generates an output at a single Decision node, Z. A layer of Hidden Nodes, h1-h4, connects the input nodes to another set of interior nodes called Class nodes c1-c2, and these then connect to the single output node, the Decision node, Z. The two layers of Hidden Nodes and Class Nodes are, in fact, both hidden. Computation occurs in each node. The structure of the node and the nature of this computation are illustrated by way of example in FIG. 12, where Z1 and Z2 are shown as inputs to respective nodes. Z1 and Z2 are each multiplied by a corresponding weight, Weight1 and Weight2. The resulting products are then added together. The sum is applied to a function block, F( ) that produces the output, Y as a function of the sum. The function F( ) may be linear, e.g., a multiple of the sum. Alternatively, F( ) could be the sign of the sum, Sgn( ) or some other non-linear function. The values of the weights in all of the nodes in a neural network are determined through the training previously mentioned. Depending upon the particular application, there may be multiple layers of hidden nodes and multiple outputs with different functions F( ).

Returning to FIG. 10, the Neural Network Component 510 operates in two possible modes: a Screening Mode and a Tracking Mode. The Screening Mode may be used during the first time the system 100 is applied to a patient. The Artificial Intelligence Subsystem 50 takes the inputs $\{E_1, E_2, \ldots, E_M\}$ and selects one of several classifications as an output. The classifications may correspond to the BI-RADS classifications previously mentioned, $B_1, B_2, B_3, B_4$ and $B_5$. The classifications made during the Screening Mode will be referred to as the "initial BI-RADS decision."

The Tracking Mode is used if the system 100 has been previously applied to the patient and a course of therapy has commenced. Here the inputs include EA(f) samples taken during the present use of the system, and are therefore denoted by $\{E^P_1, E^P_2, \ldots E^P_M\}$—the superscript "P" indicating present use. The inputs also include EA(f) samples taken during previous uses, e.g., $\{E^1_1, E^1_2, \ldots E^1_M\}$, $\{E^2_1, E^2_2, \ldots E^2_M\}$, etc. where the superscript "1" indicates the first use, "2" indicates the second use, etc. These additional sets of inputs are obtained from the Archive 60. The Tracking Mode also produces the BI-RADS classifications previously mentioned, $B_1$, $B_2$, $B_3$, $B_4$ and $B_5$. Again this will be referred to as the "initial BI-RADS decision."

At the left of FIG. 10 are the current ESD spectral samples after gap filling, $\{E^P(f)\}$. This corresponds to the Screening Mode. If operation were in the Tracking Mode the inputs would further include previous spectral samples, $\{E^1\}$, $\{E^2\}$, etc. However, in order to simplify the discussion, and without loss of generality, only operation with respect to the Screening Mode will be discussed. The samples in the set $\{E^P(f)\}$ are provided to both the Neural Network Component 510 and the Expert System Component 520.

Figure 13:
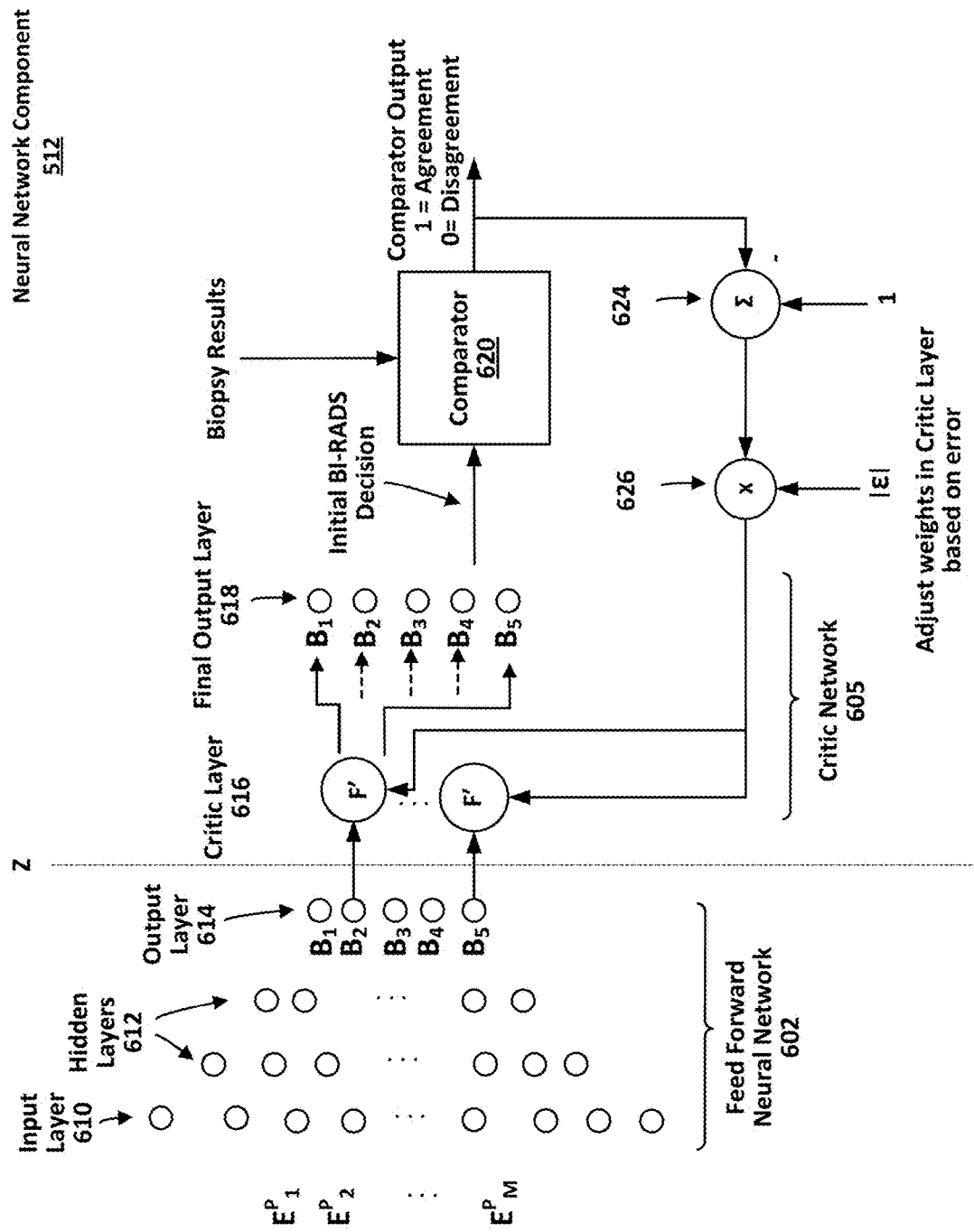
FIG. 13 shows a neural network component of an artificial intelligence subsystem according to an example embodiment of the present invention.

FIG. 13 shows an example embodiment of a Neural Network Component 512, which is partitioned by a vertical line Z-Z'. To the left of Z-Z' is a four layer "Feed Forward Neural Network" 602. To the right of Z-Z' is a two layer "Critic" Network 605. The Critic Network 605 is a standard neural network, but its computational function, F'( ) and training will be different from that of the Feed Forward Neural Network 602. The Critic Network 605 takes the output of the Feed Forward Neural Network 602 and "fine tunes" it so as to avoid giving an ambiguous BI-RADS classification. It is trained by comparison with biopsy results. The Critic Network 065 requires only a hidden layer and an output layer because there is no need of an input layer, as inputs are provided directly from the output layer of the Feed Forward Neural Network 602.

The current inputs $\{E^P_1, E^P_2, \ldots, E^P_M\}$ are supplied to the Feed Forward Neural Network 602. The number "M" of inputs depends upon certain variables such as the number of incident laser wavelengths. For purposes of this description a value of M=120 can be considered exemplary and might correspond to twenty wavelength samples from each of the six individual laser bands.

The Feed Forward Neural Network includes four layers: an Input Layer 610, two Hidden Layers 612, and an Output Layer 614. The Input Layer 610 may include a separate node for receiving each of the M inputs, e.g., 120 nodes. The number of nodes is reduced in a "pyramid" fashion towards the output side of the Feed Forward Neural Network, e.g., from 120 nodes in the Input Layer 610 to 5 nodes on the Output Layer 614. In this example, the leftmost Hidden Layer 612 might have 50 nodes and the rightmost Hidden Layer 612 might have 20 nodes. This pyramid structure mimics pattern recognition abilities of the human brain, which first looks for a larger pattern and then concentrates on successively smaller patterns within the larger pattern. The nodes of the various layers can be fully connected from a graph theory perspective. However, alternative embodiments may not have full connectivity.

Figure 12:
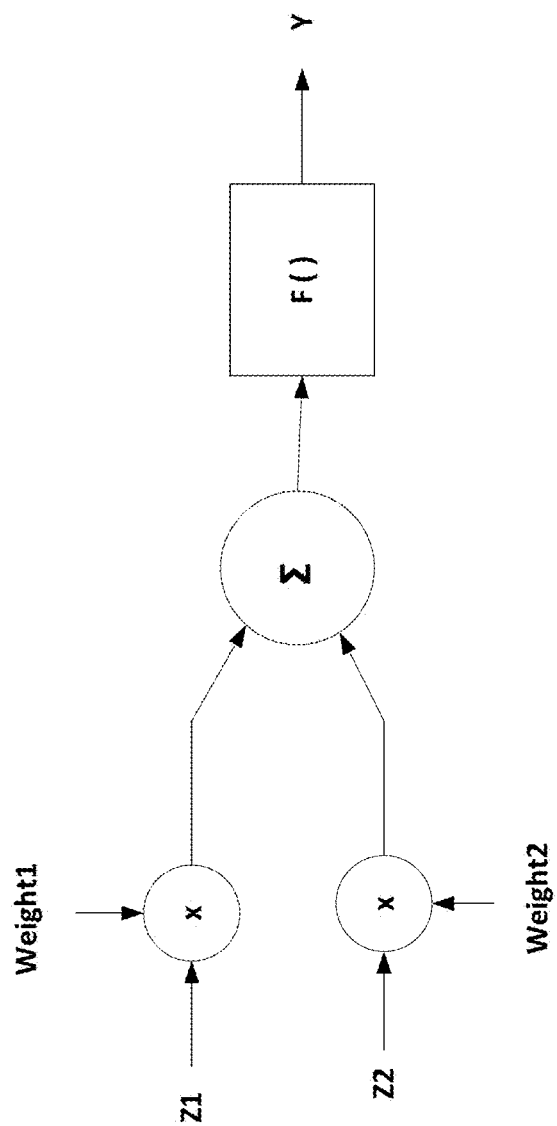
FIG. 12 is a block diagram of computation elements within a node in an example neural network.
Figure 14:
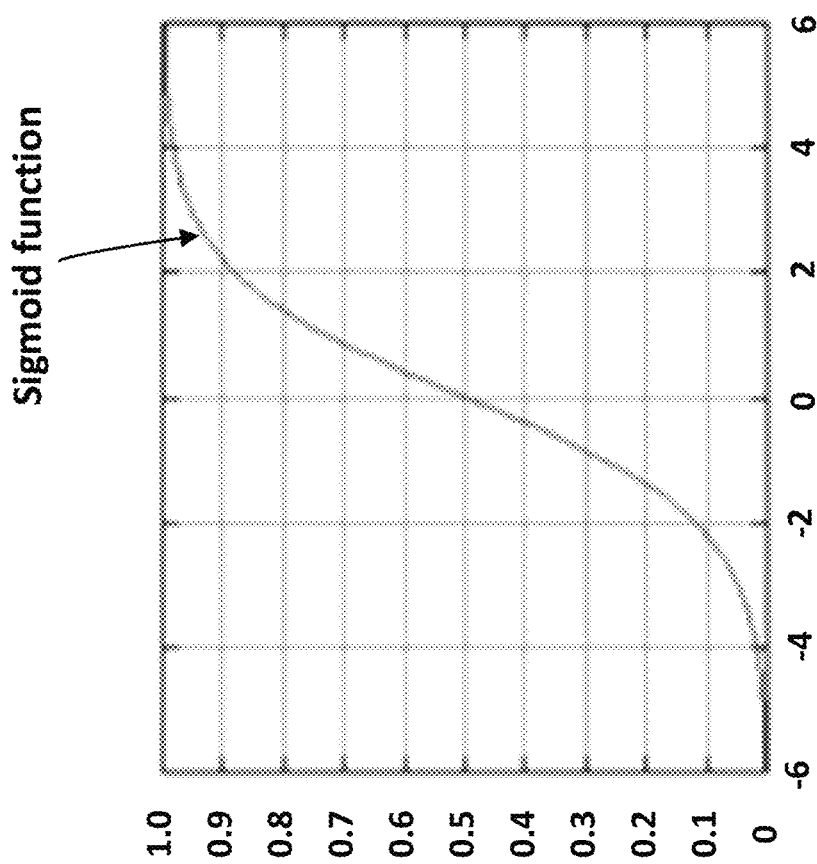
FIG. 14 shows an example of a sigmoid function.

Each node computes the F( ) function of FIG. 12, for example, as a Sigmoid Function shown in FIG. 14. The Sigmoid function is defined as Sigmoid $(x)=(1+e^{-x})^{-1}$ and has the following property: (Sigmoid $(x))'$= Sigmoid$(x)$ $(1-$Sigmoid$(x))$, where the prime symbol (') indicates taking the derivative with respect to x. This property eases the burden in computing and updating the neural network weights during a training period in which a backpropagation algorithm is used.

Neural Network Component 512 is trained before putting it into active use. First, the Feed Forward Neural Network 602 is trained as if the Critic Network 605 were not present. This training occurs during a time period referred to herein as "Cycle 1." The training data during Cycle 1 only has to relate the spectral data, $\{EA\}$ to corresponding BI-RADS classifications. No corresponding biopsy classifications are needed. Because the computations carried out during Cycle 1 may be numerous, it may be appropriate to have these computations carried out offline so that the final neural network weights for the Feed Forward Network 602 are downloaded to the system 100. In this way the computations could be carried out by Cloud computing and the training data itself would be obtained from remote databases accessed through the Internet and the Cloud. The corresponding weights settle at equilibrium values capable of providing reasonable BI-RADS decisions that can be refined as discussed below.

The training of the Critic Network 605 begins after the Feed Forward Neural Network 602 is trained and occurs during a Cycle 2. Alternatively, offline training can be performed in a similar manner to the offline training described above. The training of the Critic Network uses a different type of training data than the Feed Forward Neural Network. The training data in this instance relates the spectral data, $\{EA\}$ to corresponding BI-RADS classifications and also to known biopsy classifications of the corresponding patients. The Critic Network 605 initially passes the BI-RADS decision from the Output Layer 614 straight through a Final Output Layer 618 to a Comparator 620, which compares the decision with a corresponding biopsy decision. An error metric "c" is obtained from the comparison. If there is agreement between the biopsy decision and the BI-RADS decision the error metric will be equal to zero. Otherwise, the error metric can be a non-zero number whose exact value will depend upon the specific design of the Neural Network Component.

The absolute value of the error metric, $|\epsilon|$ is fed back during Cycle 2 to adjust the weights in the Critic Layer 616, producing a new BI-RADS decision for input to the Comparator 620. The feedback path is illustrated as including a subtraction unit 624 that subtracts the comparator output from a value of "1" and a multiplier 626 that multiplies id by the output of the subtraction unit 624. Cycle 2 training continues until a sequence of ICI's are obtained which are below some pre-set value. When this is achieved, Cycle 2 is considered complete. The Neural Network Component 512 can now be used for active, in contrast to training, operation. Although only the Critic Layer 616 is adjusted in this example, in alternative embodiments the error metric might be fed back to both the Critic Layer 616 and the Hidden Layers 612 in order to improve sensitivity and specificity, though at a cost of increased computation during training.

During active operation, the components to the right of the Final Output Layer 618 are essentially disconnected so that there is no feedback path to the Critic Layer 616. Thus the "raw" or unprocessed BI-RADS decision produced by the Feed Forward Network 602 will not cause further training of the Critic Network 605. With the feedback path removed, the BI-RADS decision produced by the Output Layer 618 can be provided to the Expert System Component 520 as the initial BI-RADS decision in FIG. 10.

Figure 15:
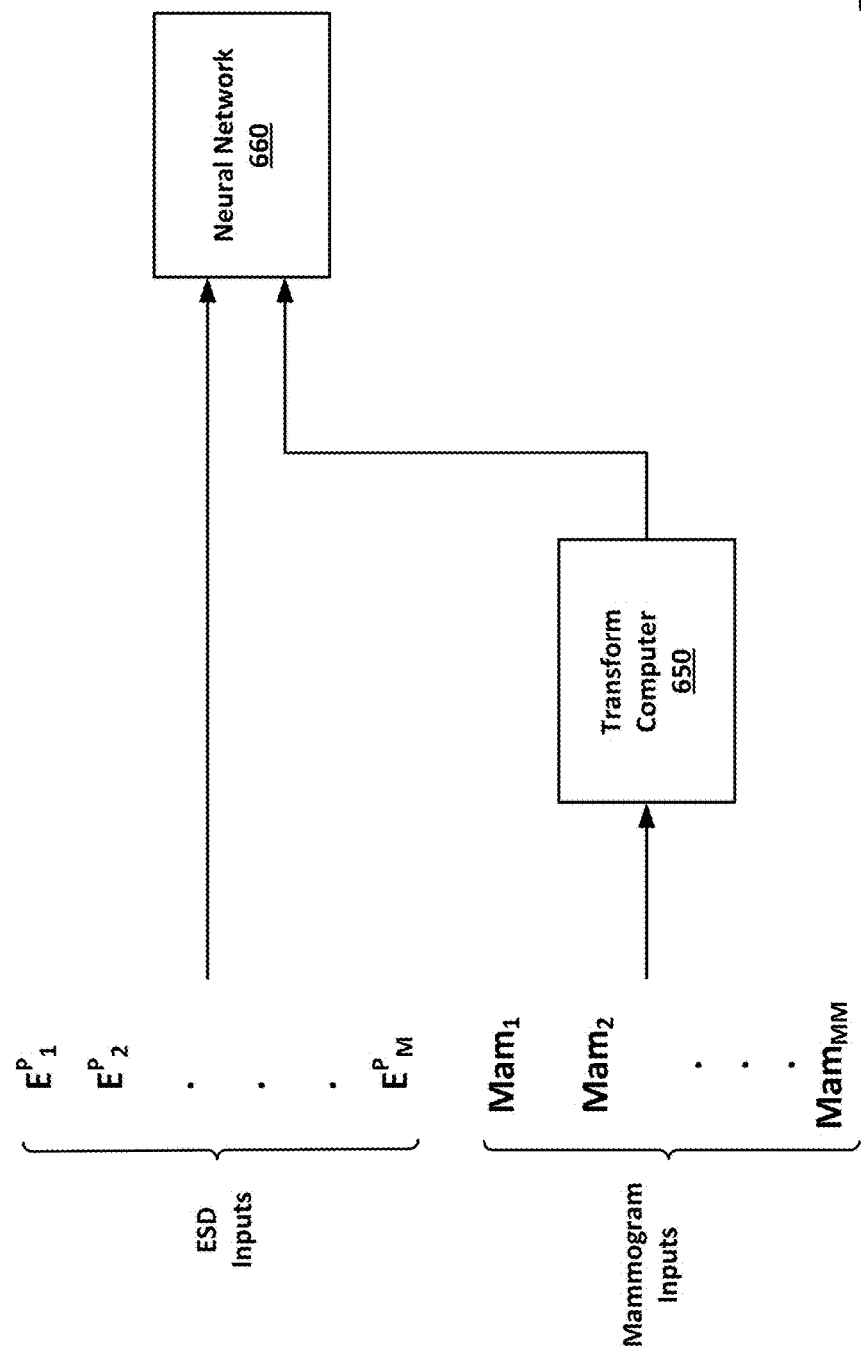
FIG. 15 shows a neural network component of an artificial intelligence subsystem according to an example embodiment of the present invention.

FIG. 15 shows an example embodiment of a Neural Network Component 514 in which the sampled ESD inputs $\{E^P_1, E^P_2, \ldots, E^P_M\}$ are considered along with inputs from a mammogram image of the patient of interest. The mammogram inputs are spatial samples of the mammogram image and are denoted as $\{Mam_1, Mam_2 \ldots Mam_{MM}\}$, where "MM" is an integer greater than or equal to one. The mammogram samples are first provided to a Transform Computer 650 that computes a spatial transform of the mammogram samples, making the mammogram samples more amenable for feature discrimination/pattern classification by a Neural Network 660. By way of example, this spatial transform could be a Fourier Transform or a Hadamard Transform. The combined inputs including $\{E^P_1, E^P_2, \ldots, E^P_M\}$ and the transformed versions of $\{Mam_1, Mam_2, \ldots, Mam_{MM}\}$ are provided to an input layer of the Neural Network 660.

The Neural Network 660 may operate in a manner similar to that of the Feed Forward Neural Network 602 in FIG. 13, described above. In another embodiment, the Neural Network 660 could be implemented with a different architecture that uses additional inputs from two-dimensional imaging techniques besides mammograms, such as those available from MRI or ultrasonography.

Figure 16:
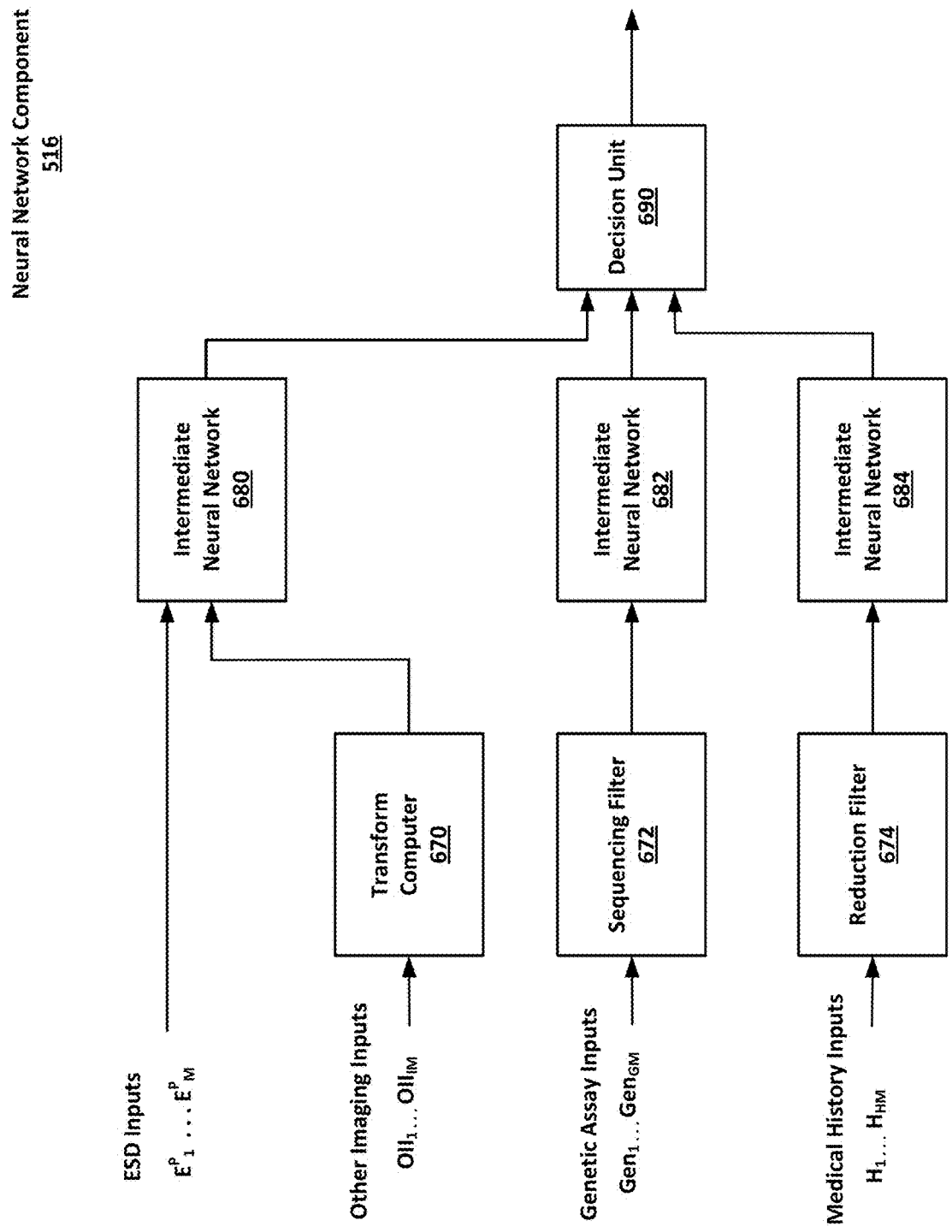
FIG. 16 shows a neural network component of an artificial intelligence subsystem according to an example embodiment of the present invention.

FIG. 16 shows an example embodiment of a Neural Network Component 516 which includes a Transform Computer 670 that computes a spatial transform of samples from other imaging techniques, similar to the processing performed by the Transform Computer 650 in FIG. 15. The transformed samples are combined with the sampled inputs $\{E^P_1, E^P_2, \ldots, E^P_M\}$ to form inputs to an Intermediate Neural Network 680 that generates its own BI-RADS outputs.

Additionally, the Neural Network Component 516 expands on the Neural Network Component 514 by adding two classes of inputs. The first class describes the genetic assay of the patient of interest. However, the first class of inputs could be enlarged to include other biomarkers that indicate the presence of cancer. The second class describes the medical history of the patient and/or the patient's family.

Genetic assay inputs are not necessarily restricted to nuclear DNA. Mitochondrial DNA is more susceptible to mutations due to limited repair mechanisms compared to nuclear DNA. Consequently, changes to the mitochondrial genes could contribute to the development of breast cancer. A Sequencing Filter 672 separates out those subsequences of the nucleotides in the DNA, which are known to have mutations corresponding to the presence of breast cancer. The output of the Sequencing Filter 672 is presented, in an appropriate numerical format, as inputs to an Intermediate Neural Network 682 that generates its own BI-RADS outputs.

A Reduction Filter 674 processes medical history inputs to separate out those items in the medical history which relate to cancer, in particular, breast cancer. These are then presented, in an appropriate numerical format, as inputs to an Intermediate Neural Network 684 that generates its own BI-RADS outputs.

Any of the Intermediate Neural Networks 680 to 684 can be calibrated to biopsy decisions in the same manner described earlier. A Decision Unit 690 forms a final decision for the BI-RADS classification from the various intermediate BI-RADS outputs. There are several ways in which the Decision Unit might operate. By way of example, Decision Unit 690 may operate by simple majority vote so that the final decision corresponds to a BI-RADS classification output by more than half of the Intermediate Neural Networks 680 to 684. Alternatively, Decision Unit 690 might form the final decision using yet another neural network. Thus, the Decision Unit 690 can be hardware and/or software based.

Returning to FIG. 10, the Expert System Component 520 accepts the initial BI-RADS decision as input along with $\{E^P(f)\}$, and possible additional inputs (if available) related to the medical history of the patient of interest. The medical history data may include previous imaging data, $\{E^1_1, E^1_2, \ldots E^1_M\}$, $\{E^2_1, E^2_2, \ldots, E^2_M\}$, etc., the BI-RADS classifications corresponding to these previous imaging data, other imaging data associated with the patient of interest (e.g., mammograms), data obtained from daily monitoring (e.g., pulse rate or blood pressure), data collected during the patient's last general physical examination (e.g., an electrocardiogram), and genetic expression assay or tumor surface receptor testing results. The medical history data may also include data concerning the patient's family.

The Expert System Component 520 also has a communication link (e.g. via the Internet) to outside data sources, which include remote databases storing large quantities of "Big Data" (e.g., imaging data for other patients, statistical analyses of imaging or other medical data for other patients, and medical literature) and remotely located human experts. These outside data sources are not necessarily mutually exclusive, as some outside data sources may combine several of the above mentioned types of Big Data or combine Big Data with manual input from a human expert. The Expert System Component 510 can send a query to any of these outside data sources, the query including the initial BI-RADS decision and the $\{EA(f)\}$ samples, and requesting an opinion on the corresponding appropriate BI-RADS classification. The outside data sources can send corresponding opinions in an automated reply or, in the case of a human expert, a manual reply. The Expert System Component 520 can read the replies via computer, for example, using a text analysis program. The Expert System Component 520 thus has many inputs. The Expert System Component 520 then takes all of its inputs and uses a program employing rule-based logical reasoning to refine the initial BI-RADS decision, producing a final BI-RADS decision as an output decision. The final BI-RADS decision may include a BI-RADs classification together with a corresponding confidence level. The measure of confidence could be on a range from 0 to 100 with 0 representing no confidence and 100 representing complete confidence. By way of example, the confidence or trust in the output provided by the Expert System Component 520 can be derived in connection with the scoring and thresholding described below.

Unlike neural networks, expert systems do not have to be trained, but rather model the reasoning employed by a human expert as a computer algorithm that produces the determination. A great deal of progress has been made in the development of expert systems due to increases in the speed and memory of computers, the organization of the hierarchy of databases and the ability of computers to extract knowledge directly from text without much manual intervention. Although the expert's reasoning has been automated, the expert may still play a role in the determination process by, for example, manually identifying appropriate data sources, which can be stored in the Archive 60.

The Expert System Component 520 has within it a computer program which executes algorithms that use rule based logical reasoning to generate the final BI-RADS decision from the program inputs. This rule based logical reasoning is based upon modelling the decision process of a human expert when given the same inputs as the Expert System Component and asked to come up with a final BI-RADS decision. For example, a human expert might be a radiologist specializing in breast cancer, and the program could match all of the Expert System Component inputs to a template that the radiologist might use in making a BI-RADS decision. As another example, the program could perform a statistical analysis that the radiologist might use when presented with all of the inputs (include those derived from Big Data) and come up with a most likely BI-RADS decision. The Expert System Component 520 thus operates by fusing many types of input data, making use of Big Data available from remote sources via the Internet, in combination with a rule based logical reasoning program that models the analytical processes that a human expert would employ to come up with the final BI-RADS decision.

The initial BI-RADS decision can include one of the BI-RADS classifications: $B_0$—"incomplete," $B_1$—"negative," $B_2$—"benign findings," $B_3$—"probably benign," $B_4$—"suspicious abnormality," $B_5$—"highly suspicious of malignancy" and $B_6$—"known biopsy with proven malignancy." In the example of FIG. 10, $B_0$ and $B_6$ are not used. One objective of the Expert System Component 520 is to take ambiguous BI-RADS classifications ($B_3$ and $B_4$) and, using other inputs and rule-based logic, move these ambiguous classifications to one of the unambiguous categories, e.g., $B_1$ or $B_5$. This is important because leaving a BI-RADS classification in an ambiguous category may ultimately result in biopsies which are not needed, leading to unnecessary anxiety, expense and inconvenience for the patient.

As noted earlier, the rule based logic can model human experts in how they would deal with the input data. A first step in doing this modelling is to have the Expert System organize its inputs in the same way that the human expert would. Specifically, a human expert can be assumed to organize the input data hierarchically, with some input data being classified as very important, some important, and others being less important or of no consequence. The Expert System can proceed likewise. By way of example, a possible organization of the different input data might be, in order from most to least important:

1. Sequence of previous BI-RADS decisions for the patient
2. Corresponding sequence of $\{EA(f)\}$'s
3. Sequence of previous BI-RADS decisions for the patient from other imaging techniques
4. Patient's individual medical history, including incidence of other cancers
5. Patient's family medical history, including incidence of other cancers
6. Results of a genetic assay on the patient
7. EKG results from the patient's last physical examination
8. Pulse rate from the patient's last physical examination Examples of algorithms that apply rule based logic to organized input data are now described. Each algorithm represents a different modelling of the logical processes of a human expert, such as a radiologist, in considering the input provided. These example algorithms encompass the logical processes carried out in the great majority of clinical scenarios. The expert systems described herein may execute any of the algorithms below, and can be implemented at least partially as software written in a computer programming language such as LISP, CLIPS (C Language Integrated Production System) or PROLOG.

Figure 17:
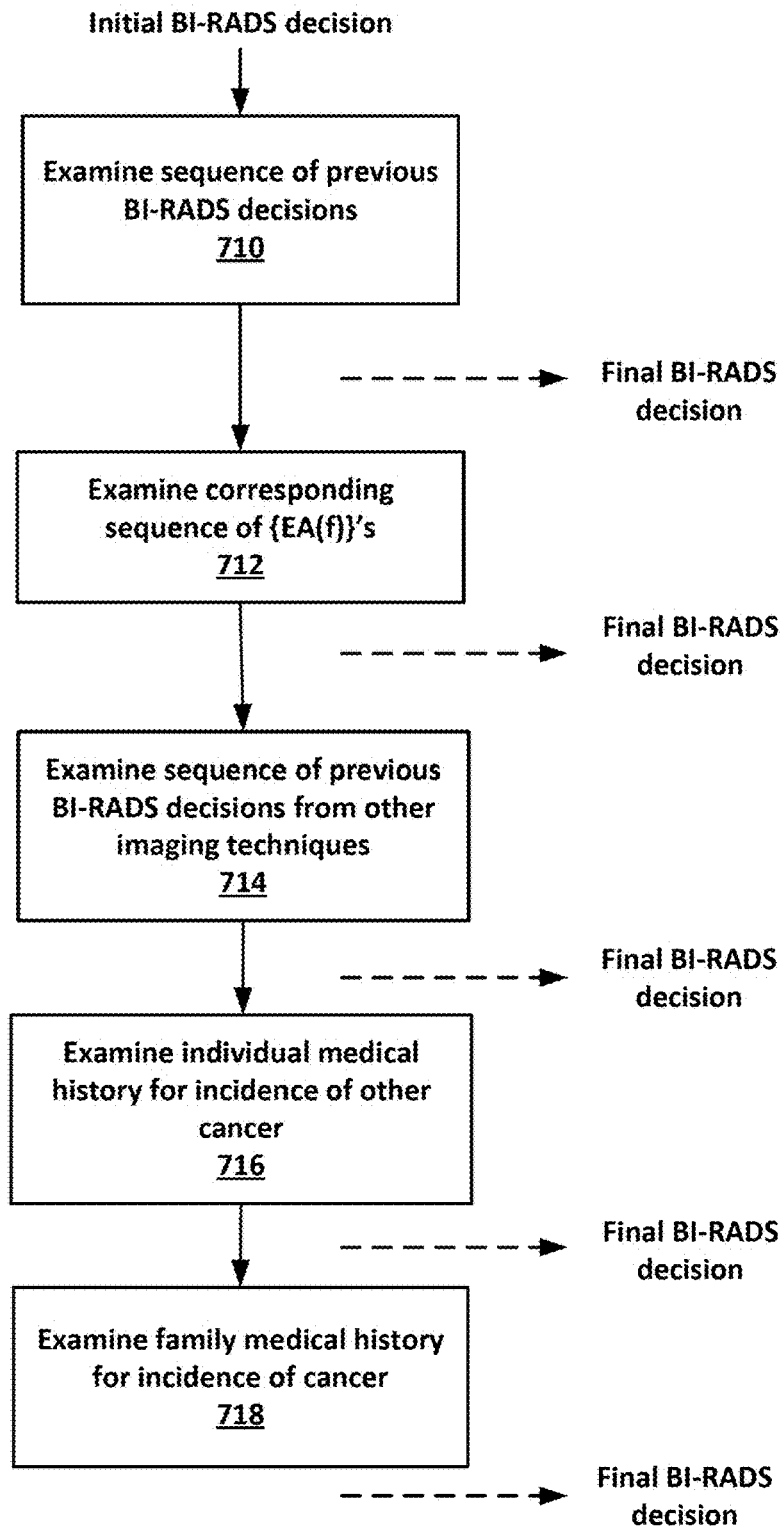
FIGS. 17 to 20 each show an algorithm, executed by an expert system, according to an example embodiment of the present invention.

FIG. 17 shows an example embodiment of an algorithm 700, referred to herein as a "Sequential Decision Algorithm." The input from the Neural Network Component is provided at the top. By way of example, suppose the input includes the classification: $B_4$—"suspicious abnormality." In step 710, the algorithm determines if there exists a sequence of previous BI-RADS decisions for this patient. If there are many previous decisions in sequence (a "long string") and indicating probable malignancy (e.g., $B_4$ or $B_5$ classifications), the algorithm might decide that there is a very high probability of a malignancy and upgrade the decision to $B_5$—"highly suspicious of malignancy" before terminating the algorithm (termination is indicated by an arrow to the right).

On the other hand, if this is the first time that the patient has presented with a $B_4$—"suspicious abnormality," the algorithm continues to the step 712, where the spectral data $\{EA(f)\}$ corresponding to this BI-RADS classification is examined. Here, the algorithm might use results obtained from queries to Big Data to learn that the spectral data is sufficiently close to qualifying as a $B_5$—"highly suspicious of malignancy" classification, in which case the classification in the initial BI-RADS decision, referred to herein as the "initial classification," is upgraded to $B_5$ before terminating the algorithm.

If the initial classification is not sufficiently close to the next classification, the algorithm proceeds to step 714, examines a sequence of previous BI-RADS decisions obtained for the patient using other imaging techniques (e.g., MRI or mammography). Similar to step 710, if there are many previous decisions indicating probable malignancy, the initial classification may be upgraded to $B_5$ before termination.

If there is no sequence of previous BI-RADS decisions in step 714 or the previous sequence is inconclusive as to probable malignancy, the algorithm proceeds to step 716, where it examines the patient's individual medical history to determine whether there exist sufficient incidences of other cancer or other medical indicators that justify upgrading the initial classification.

Finally, the algorithm may proceed to step 718 if there is insufficient or inconclusive individual medical history. In step 718, the algorithm examines the medical history of the patient's family for incidence of cancer or other medical indicators. For example, the algorithm might find that the patient's mother, grandmother and sisters all had breast cancer, in which case the initial classification is upgraded before termination.

Thus, the algorithm 700 can sequentially step through different data sources, making a decision at each step to rule out or confirm the presence of a malignancy based on the data at the particular step. If the algorithm proceeds through all of the steps without upgrading an initial classification, the algorithm may leave the initial classification the same. Alternatively, the algorithm may decide that given the lack of support in the other input data at steps 710 to 718 for upgrading the initial classification, the classification can be downgraded, e.g., from $B_4$ to $B_3$. An initial classification may also be downgraded to a classification that is less indicative of cancer if at least one data source indicates that cancer is unlikely.

Figure 18:
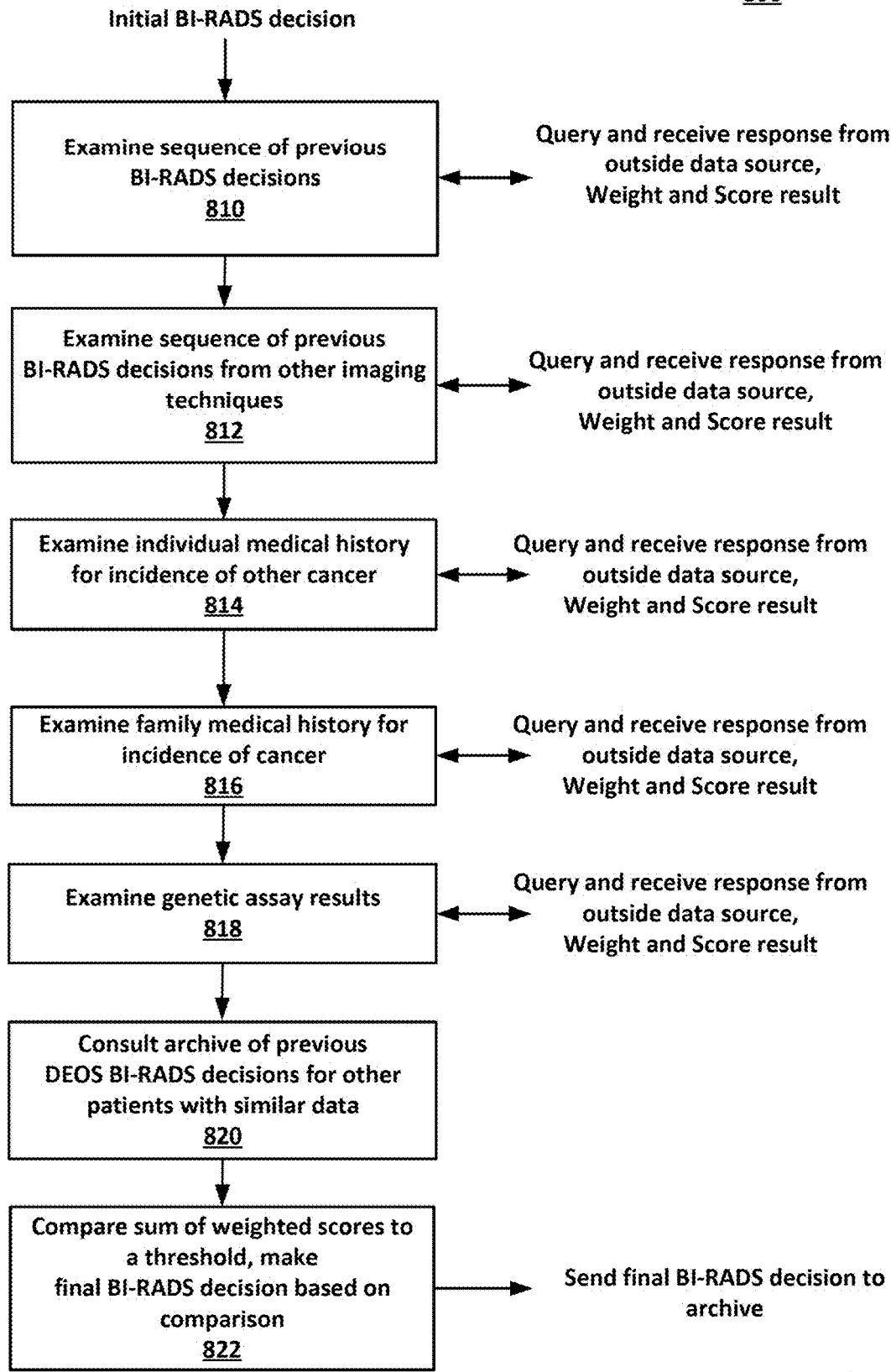

FIG. 18 shows an example embodiment of an algorithm 800, referred to herein as a "Cumulative Threshold Decision Algorithm." As with the example of FIG. 17, suppose that the input is $B_4$—"suspicious abnormality." Step 810 is similar to step 710 in that the algorithm examines a sequence of previous BI-RADS decisions for this patient. However, in contrast to the algorithm 700, if there is a long string of malignancy indicative decisions, the algorithm 800 does not automatically upgrade the initial classification, but instead consults an outside source residing in Big Data. Thus, in step 810, the algorithm may send a query to the outside data source, providing the outside data source with the sequence of previous BI-RADS decisions, the initial BI-RADS decision, and possibly the current $\{EA(f)\}$ samples, and requesting an opinion which is returned in a computer-readable format, e.g., read using a computerized text analysis program.

The algorithm then tags the initial BI-RADS decision with a score indicating the likelihood of there being a "highly suspicious" malignancy. The score could, for example, be any number from 0 to 10, with 0 representing a definite "It is NOT" and 10 representing a definite "It is."

The algorithm could also attach a weight to the score based on the relative importance of the data used in step 810 compared to data used in the other steps. For example, the weight could be a number from 1 to 5, with 1 representing "Of No Importance" and 5 representing "Of Most Significant Importance."

Similarly, steps 812 to 818 may each involve consulting an outside data source by providing the outside data source with the initial BI-RADS decision, the current {EA(f)} samples, and another set of cancer-relevant medical data, then computing a score based on a response from the outside data source, with or without an attached weight. In step 812, the algorithm examines a sequence of previous BI-RADS decisions obtained for the patient using other imaging techniques, similar to step 714.

In step 814, the algorithm examines the patient's individual medical history for incidences of other cancer, similar to step 716.

In step 816, the algorithm examines the medical history of the patient's family for incidences of cancer, similar to step 718.

In step 818, the algorithm examines results of a genetic assay on the patient for cancer indicators.

No DEOS spectral data is examined in steps 812 to 818 because algorithm 800 models the logical processes of a human expert, such as a physician unfamiliar with DEOS spectral data in it raw, unprocessed form.

In step 820, the algorithm consults an archive within the system, e.g., Archive 60. The archive stores BI-RADS results of all previous patients that have been considered. The algorithm may fetch from the archive results of other patients having similar imaging data, medical history and genetic assay as the data processed in the earlier steps. Once this other patient data is received, the algorithm computes a score indicating the likelihood of the classification for this particular patient being a "highly suspicious" malignancy and may attach a corresponding weight.

In step 822, the algorithm computes a weighted average from all of the scores and weights. The algorithm then compares the weighted average to a set threshold in order to make a final BI-RADS decision. If the weighted average is equal to or exceeds the threshold, then the initial classification is changed to "highly suspicious." If the weighted average is less than the threshold, then the initial classification remains unchanged. In either case, the data on the particular patient of interest and the final BI-RADS decision are provided to the internal archive.

Figure 19:
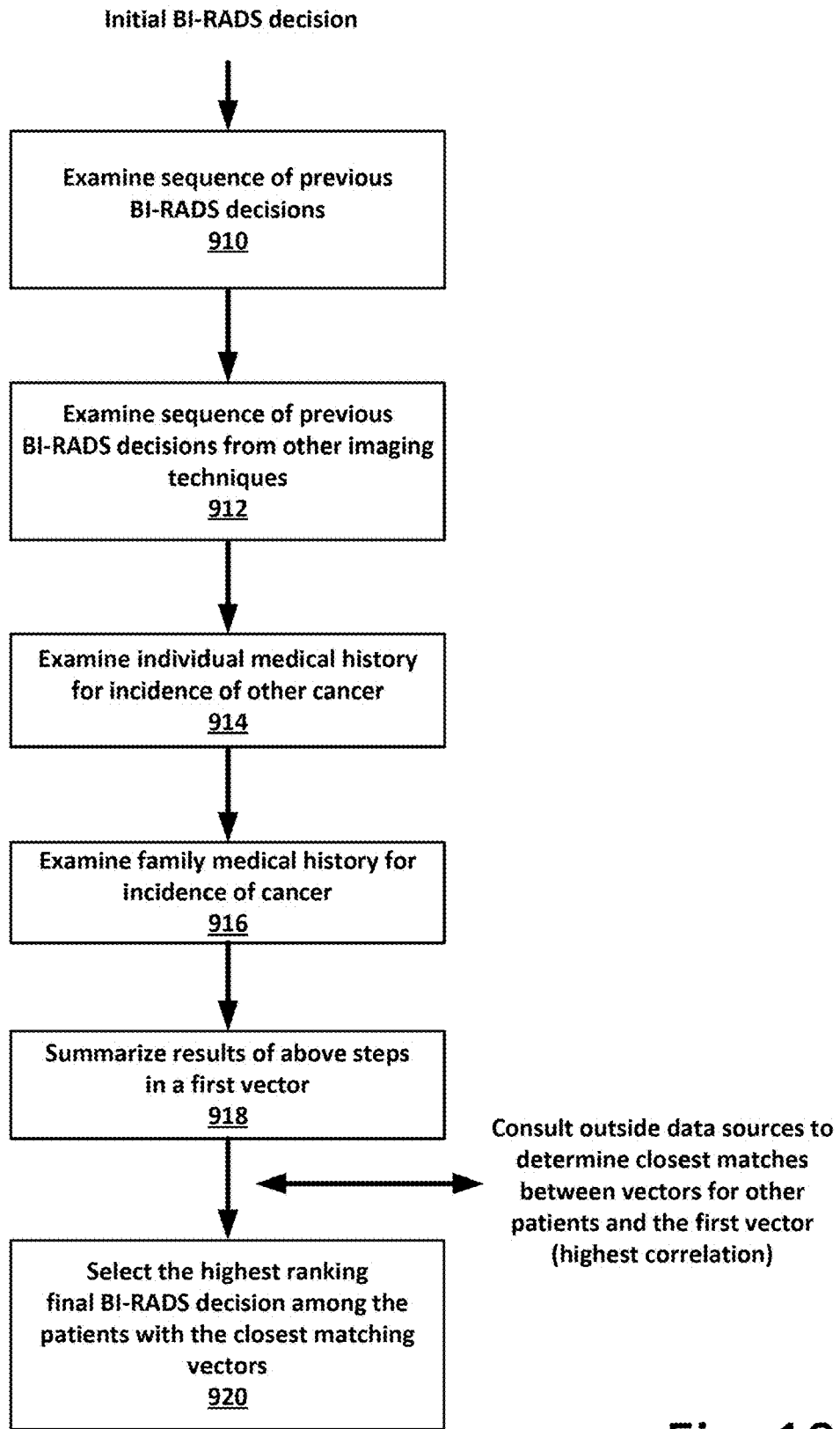

FIG. 19 shows an example embodiment of an algorithm 900, referred to herein as a "Correlative Coding Decision Algorithm." As before, by way of example, suppose the input is $B_4$—"suspicious abnormality." In step 910, the algorithm examines a sequence of previous BI-RADS decisions for the patient.

In step 912, the algorithm examines a sequence of previous BI-RADS decisions obtained for the patient using other imaging techniques.

In step 914, the algorithm examines the patient's individual medical history for incidences of other cancer.

In step 916, the algorithm examines the medical history of the patient's family for other incidences of cancer.

In step 918, the algorithm collects and summarizes results from steps 910 to 916 by coding the results together with the initial BI-RADS decision into a first vector containing binary components. The algorithm then contacts outside data sources to obtain the same data from a population of other patients, the data including final BI-RADS decisions that have been generated for those other patients. The algorithm codes this other patient data in additional vectors, then identifies those additional vectors that most closely match the first vector based on degree of correlation. The algorithm may determine a degree of correlation by computing a scalar or dot product of the first vector and an additional vector. The patients associated with the identified additional vectors form a subset of the population.

In step 920, the algorithm ranks the final BI-RADS decisions of the subset, that is, determinations that have previously been generated for those patients associated with the closest matching additional vectors. It then selects the final BI-RADS decision which has the highest rank among the subset (e.g., most votes) as its own final BI-RADS decision. There are many variations of this particular algorithm. For example, all vectors within a certain value range of the highest correlation value may be considered in step 920. As another example, the data corresponding to each of steps 910 to 916 could be weighted differently, putting a different metric on the underlying vector space. The correlation values could then be computed taking these weights into account.

Figure 20:
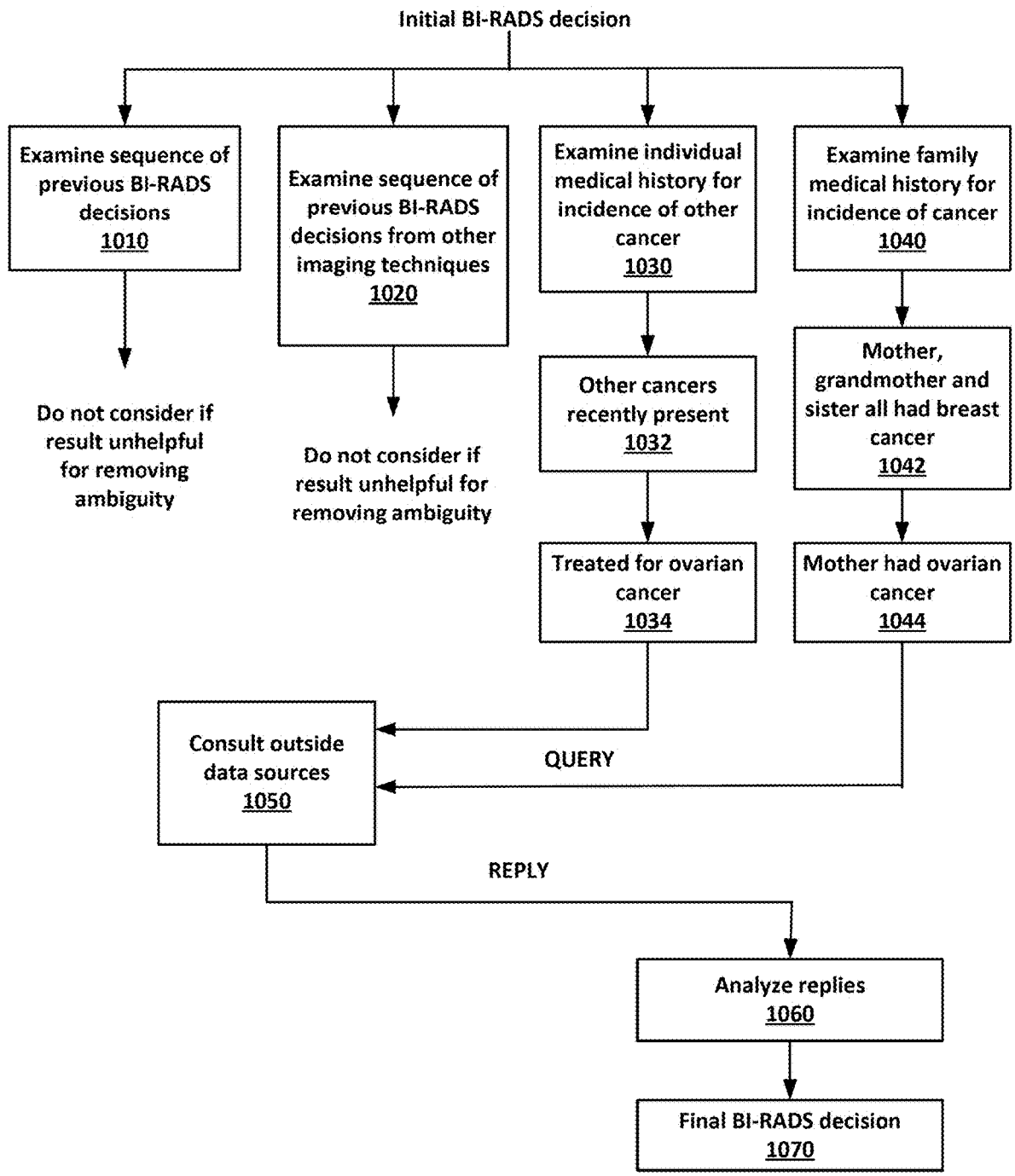

FIG. 20 shows an example embodiment of an algorithm 1000, referred to herein as a "Purge and Develop Algorithm." Algorithm 1000 simulates the logical deductive reasoning of a physician who may very quickly see that certain information presented is clearly not helpful for resolving the problem of ambiguity and therefore discards such unhelpful information. As before, by way of example, suppose the input is $B_4$—"suspicious abnormality." Algorithm 1000 differs from the earlier described algorithms in that steps 1010, 1020, 1030 and 1040—while numbered essentially in a hierarchical order—are performed simultaneously and consider the input data in a cursory fashion compared to the counterpart steps in the earlier algorithms.

In step 1010, the algorithm examines a sequence of previous BI-RADS decisions for the patient.

In step 1020, the algorithm examines a sequence of previous BI-RADS decisions obtained for the patient using other imaging techniques.

In step 1030, the algorithm examines the patient's individual medical history for incidences of other cancer.

In step 1040, the algorithm examines the medical history of the patient's family for other incidences of cancer.

In each of steps 1010, 1020, 1030 and 1040, if the corresponding result is incapable of removing an ambiguity in the initial classification, the result is purged from further consideration. Thus, steps 1010, 1020, 1030 and 1040 provide an initial filtering of the input data. By way of example, FIG. 20 shows the purging for steps 1010 and 1020, but not the remaining steps 1030 and 1040. Suppose that steps 1010 and 1020 each output a $B_4$ classification and yield no further information. Any processing steps located in the paths below steps 1010 and 1020 are essentially abandoned and the corresponding information is discarded.

After discarding a result, the algorithm then considers in order from left to right the remaining examination steps (1030 and 1040). Each of these remaining steps may lead to further examination steps in which the corresponding medical histories (individual or family) are investigated in greater detail. For example, the algorithm may discover in step 1032 that the patient was recently diagnosed as having other cancer(s). Investigating further in step 1034, the algorithm may discover that the patient was treated for ovarian cancer.

The algorithm may also discover in step 1042 that the patient's mother, grandmother and sister all had breast cancer, and in step 1044 that the mother had ovarian cancer.

After obtaining the additional information in steps 1032, 1034, 1042 and 1044, the algorithm sends this additional information in a query to outside data sources, including databases represented by Big Data and expert consultants (step 1050).

In step 1060, the algorithm receives and analyzes replies from the outside data sources. The replies can be in a computer-readable format such as a text document that can be analyzed by computer.

In step 1070, the algorithm outputs a final BI-RADS decision based upon the analysis of the replies.

Presentation Subsystem

The Presentation Subsystem 70 provides results concerning cancer detection or success of therapy to the physician, in a manner that is easy for a physician with no engineering or imaging background to understand. In particular, the Presentation Subsystem 70 may include a graphical display device that shows the area of the breast which is illuminated (e.g., a graphical representation of the breast area), in conjunction with the results of the Artificial Intelligence Subsystem 50. The results may include a final BI-RADS decision, including a classification and a corresponding confidence measure.

The Presentation Subsystem 60 may include a user interface through which the physician can request information stored in the Archive 70. The requested information can be output on the graphical display and may include the raw data which led to the final BI-RADS decisions. For example, the physician may request the entire history of EA(f) functions operated on by the neural network(s) of the Artificial Intelligence Subsystem 50. The user interface may include local and/or remote components. For example, in addition to a graphical display (which is local to the physician's office or CCC), the user interface may include an Internet-based software interface that allows the physician to access the results or raw data remotely by smart phone, tablet or personal computer.

The system 100, including the Presentation Subsystem 70, can be a stand-alone device or set of connected devices. Alternatively, the system 100 can be integrated with other breast cancer screening/diagnostic techniques, such as mammography, MM, ultrasonography, thermography and irradiation by microwaves, DOS and others, thus forming a hybrid architecture in which DEOS plays an important role in cancer detection. A hybrid architecture may benefit from the economies obtained by integrating different technologies together. For example, in a hybrid architecture, the system 100 could use a camera that is already used for another screening/diagnostic technique, but for a different purpose such as photographing breast tissue. The Presentation Subsystem 70 may then overlay the photographs with internal maps indicating cancerous, non-cancerous and ambiguous areas, thereby integrating results from the System 100 with captured images of actual tissue regions.

Mitigating Noise and Interference

Noise and interference can adversely affect the ability of the system to reliably detect cancerous tissue or determine the success of a program of therapy. Such noise and interference may result from the presence of active electronic components such as mixers (e.g., mixer 222 in FIG. 4), amplifiers (e.g., LNA 290 in FIG. 6) and ADCs (e.g., ADC 316 in FIG. 7). The effects of such noise and interference can be mitigated using a number of techniques. Time diversity is one such technique and averages out the noise/interference by sending multiple copies of the same modulation waveform, but spaced apart in time.

The noise affecting the ADC can manifest itself as jitter. This can be ameliorated by using highly stable clocks. It can also be ameliorated by using time interleaved ADC streams, in which a bank of ADCs operate in parallel—each at a sub-multiple of the desired rate—and then the outputs of the ADCs are combined into one high speed sample stream. The individual lower rate ADCs have less jitter.

There may also be optical noise affecting both incident and scattered light. Optical noise can be appropriately dealt with by confining the light being delivered to and received from fiber optic cables with an appropriate mechanical and packaging configuration. This could be accomplished by having a plurality of fiber optic cables, where one cable is designated for each incident laser wavelength. Alternatively, it could be accomplished by having a single fiber optic cable which is shared by the individual lasers through a Time Division Multiplexing (TDM) or Time Division Switching scheme, where each laser has the shared fiber optic cable on a dedicated basis for a given interval of time. This sharing can also be accomplished on a wavelength basis, using a Wavelength Division Multiplexing (WDM).

TDM is an effective way to reduce the requirement for a multiplicity of fiber optic cables. However, it increases the time required in the transmission of the radiating signals and the collection of the reflected signals. This does affect the overall throughput in terms of end-to-end processing time. WDM is also effective for reducing the number of fiber optic cables and has no penalty in terms of reduction in throughput due to increased transmission and reception times. Therefore, WDM is preferred for use in connection with the example embodiments. Wavelength Division Multiplexers may be used to combine light of different wavelengths into a single fiber. Multiple wavelengths can be accommodated by WDM, in a manner similar to the frequency division multiplexing that has been used in broadcast radio systems. However, instead of operating on lower frequency radio signals, WDM operates on much higher frequency laser signals. Typically, anywhere from 4 to 24 wavelengths are combined in WDM. Therefore, the relatively small number of wavelengths required by the present cancer detection system is more than well matched to the present state of WDM technology.

With WDM the incident light from each fiber may be collimated. The collimated beams may then be combined using a dichroic filter before being focused into a target fiber. In the context of the example embodiments, the distances that the optical signals have to traverse are very small, e.g., on the order of a meter, so that amplification prior to the signals being input to a Wavelength Division Multiplexer may be unnecessary. Accordingly, the Wavelength Division Multiplexer can be implemented as a miniature circuit, the dimensions of which are on the order of a centimeter, making it well suited for placement on a printed circuit board. Such miniaturization may be accomplished using various techniques. For example, collimators with plano-convex rod lenses of different radii can be employed. Twisted and parallel fusion processes with fused biconical taper (FBT) techniques may also be employed.

The following is an example description of the type of miniature WDM arrangement that might be used in the present cancer detection system:

Number of wavelengths combined: 6
Operating wavelengths: 630 nm, 680 nm, 750 nm, 800 nm, 825 nm, 900 nm
Fiber optic cable types connected: multi mode
Fiber core/cladding size (microns): 85/125
Fiber jacket type: Hytrel Connector type: ST Back reflection level: 35 dB All of the noise mitigation techniques mentioned above may be used in the present cancer detection system in order to mitigate the effects of noise and attain more accurate results. Additionally, the Neural Network Component of the system can be adapted to further reduce noise. In the Neural Network Component 512 of FIG. 13, the inputs are $\{E^P_1, E^P_2, \ldots, E^P_M\}$. If present, noise can be represented as $\{En^P_1, En^P_2, \ldots, En^P_M\}$. Here $En^P_i$ for i=1 . . . M is a noisy version of $E^P_i$. Specifically, $En^P_i = E^P_i + n_i$ where $n_i$ is a noise sample representing the noise contributed by one or more of the above noted noise sources. The Neural Network Component 512 could make use of this noise representation if the training set is enlarged to include many "noisy" variations of each $\{E^P_1, E^P_2, \ldots, E^P_M\}$ used for training. That is, sequences of noise samples can be purposely added to each training sequence $\{E^P_1, E^P_2, \ldots, E^P_M\}$ to train the Neural Network Component to better handle noise. This approach can include the use of noise samples representing processing related noise, such as noise caused by the non-ideal behavior of the mixers and amplifiers.

Physical Configuration, Size and Portability

Figure 21:
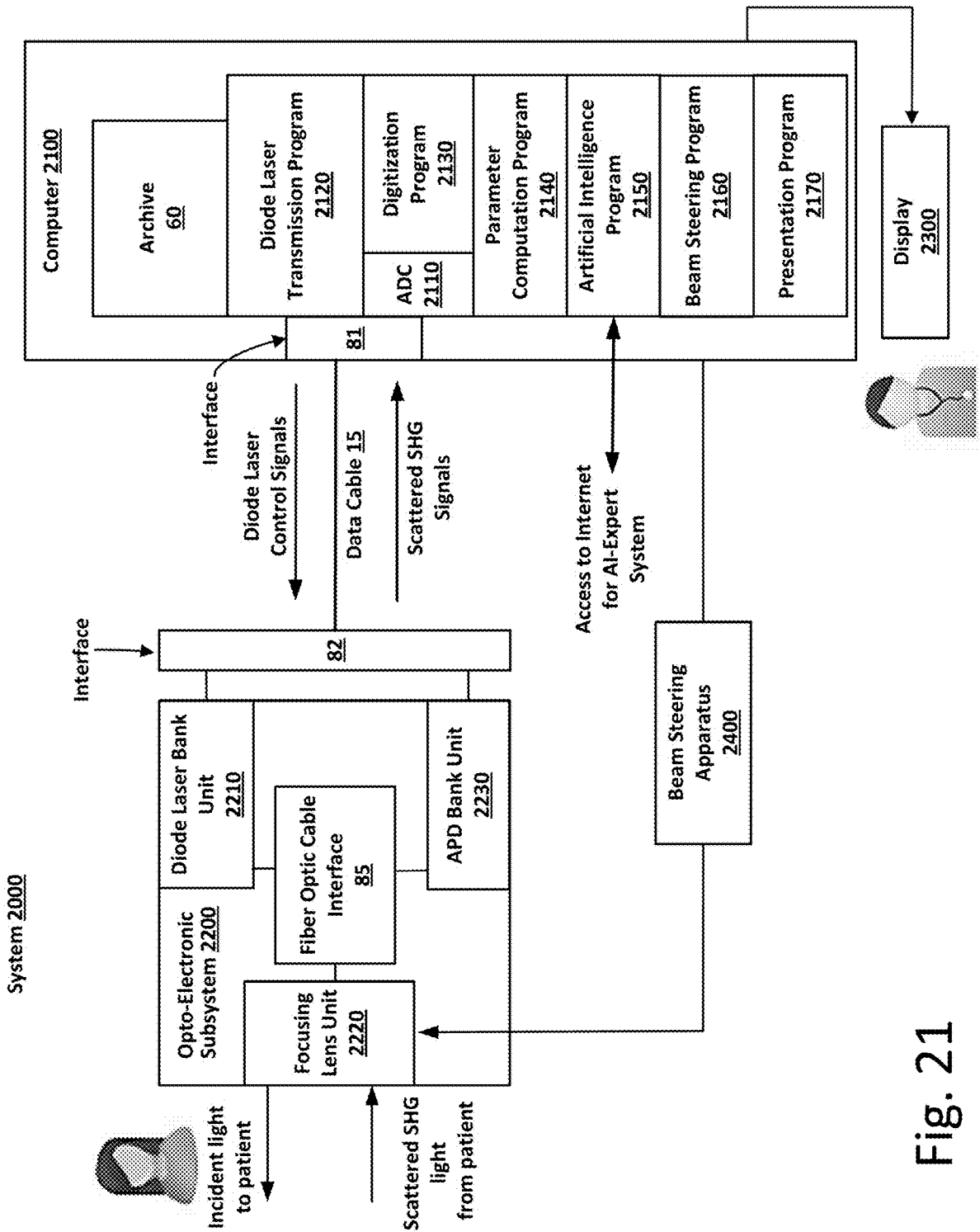
FIG. 21 is a block diagram of a system for cancer detection according to an example embodiment of the present invention.

FIG. 21 is a block diagram of a cancer detection system 2000 according to an example embodiment. The system 2000 may include the same overall structure as the system 100 in FIG. 2, and includes a computer 2100, e.g., a personal or laptop computer located at the office of a physician, an Opto-Electronic Subsystem 2200, and a display 2300. The computer 2100 includes an ADC 2110 and various software programs. The computer 2100 further includes a hardware processor executing instructions contained in the programs. The programs include a Diode Laser Transmission Program 2120, a Digitization Program 2130, a Parameter Computation Program 2140, an Artificial Intelligence Program 2150, a Beam Steering Program 2160, and a Presentation Program 2170.

Diode Laser Transmission program 2120 generates control signals for lasers in the Opto-Electronic Subsystem 2200. The lasers are located in a Diode Laser Bank Unit 2210 and receive the control signals through a cable 15 between an interface 81 of the computer 2100 and an interface 82 of the Opto-Electronic Subsystem 2200. The interfaces 81 and 82 can be serial interfaces, Universal Serial Bus (USB) interfaces, or any other conventional computing interface.

The lasers output laser light through a fiber optic cable interface 85 to a Focusing Lens Unit 2220 that concentrates the incident light and also collects the scattered SHG light reflected back from the patient. The fiber optic cable interface 85 transmits the collected SHG light to an APD Bank Unit 2230, which converts the SHG light into analog electrical signals for transmission to the computer 2100 via the interface 82.

At the computer 2100, the ADC 2110 converts the analog signals into corresponding digital signals for processing. The digital signals may be processed by the Digitization program 2130, the Parameter Computation Program 2140, the Artificial Intelligence Program 2150, and the Presentation Program 2170 in accordance with the earlier described operations of the Digitization Subsystem 30, the Parameter computation Subsystem 40, the Artificial Intelligence Subsystem 50, and the Presentation Subsystem 70 in FIG. 2. For example, the Artificial Intelligence Program 2150 may access the Internet to query an outside data source on behalf of an Expert System to generate a final BI-RADS decision, and the Presentation Program 2170 may display the final BI-RADS decision on the display 2300.

Beam Steering Program 2160 controls a Beam Steering Apparatus 2400 to steer the Focusing Lens unit 2220 over an angle to scan the entire active area. Beam steering may be realized by any one of various optical arrangements including, for example: 1) rotating mirrors connected to mechanical attenuators with electric motors and galvanometers, 2) mirrors located between two piezoelectric actuators, 3) non-flat, e.g., deformed or curved, mirrors, 4) steering devices based upon the gradient of refractive index in a liquid crystal cell with electrically controlled birefringence, 5) an optical phased array, and 6) an electro-optic scanner where the deflection angle is voltage controlled.

The system 2000 can be implemented with small components. For example, there exist suitable diode laser packages (a diode laser with an integrated control chip) and APDs, which are several times smaller in diameter than a penny coin. Additionally, suitable optical filters and lenses exist which are on the order of tens of millimeters in diameter, e.g., a 12.7 mm diameter near-infrared filter and a 25.44 mm diameter near-infrared convex lens. There are also electro-optic beam steering devices which are small enough to be held between two fingers. Therefore, even if the Opto-Electronic Subsystem 2200 were designed to include large banks of diode lasers and APDs, the overall size of the Opto-Electronic Subsystem can be made quite small. The other main component of the system 2000 is the computer 2100 and is on the order of the size of a standard personal computer. Thus, the above described systems can be made quite portable.

An example embodiment of the present invention is directed to one or more processors, which may be implemented using any conventional processing circuit and device or combination thereof, e.g., Central Processing Unit(s), Microprocessors, Field Programmable Gate Arrays (FPGAs) and other signal processing devices, to execute instructions provided, e.g., on a non-transitory, hardware-implemented computer-readable storage medium including any conventional memory device, to perform any of the methods or algorithms described herein, alone or in combination.

In the preceding specification, the present invention has been described with reference to specific example embodiments thereof. It will, however, be evident that various modifications and changes may be made thereunto without departing from the broader spirit and scope of the present invention as set forth in the claims that follow.

The embodiments described herein may be combined with each other in various combinations. For example, although the neural network component has a BI-RADS classification as its basic output, some measure of the confidence or trust in this output could also be provided by the neural network component or computed from the neural network component's output. By way of example, this confidence level could be obtained by examining the levels of the neural network output layer, and computing how close the highest output is to its nearest competitor (e.g., by comparing a value of the node in the output layer 618 producing the initial Bi-RADS classification to a value of a node in the output layer 618 that would output an opposing classification). Therefore, a neural network according to the present invention may, in addition to outputting BI-RADS classifications, be configured to produce an initial confidence level, which is then input to an expert system that refines the initial confidence level (e.g., based on the above described scoring and thresholding) to generate a final confidence level.

The embodiments described herein may be combined with embodiments described in U.S. patent application Ser. No. 14/624,190, including combining aspects of analogous system components. For example, an expert system according to the present invention may implement the Purge and Develop algorithm 1000 using Cloud computing to divide the reading of cancer-relevant medical data into subtasks (e.g., corresponding to steps 1032, 1034, 1042 and 1044), then perform a quick, non-exhaustive reading of the material corresponding to the respective subtasks, and purge those subtasks that do not yield relevant material, i.e., material that is unhelpful for resolving an ambiguous classification, as explained with respect to steps 1010 and 1020.

As another example, the DOS techniques disclosed in U.S. patent application Ser. No. 14/624,190 could be combined with the DEOS techniques in the present disclosure, with the DOS techniques providing another source of image data for making BI-RADS decisions. This combination is quite feasible as the same laser or set of lasers could be used to produce light in the near infrared spectrum for DOS as well as DEOS purposes. Other components could also be shared including, for example, APDs, mixers, ADCs and amplifiers.

The specification and drawings are accordingly to be regarded in an illustrative rather than restrictive sense.

What is claimed is:

1. A device comprising:
   a processor;
   a memory which stores an artificial intelligence subsystem;
   a display;
   a beam steering apparatus configured to steer a focusing lens and a collection lens over an angle to scan an active area using a Stepped Raster Scanning (SRS) technique, Digital Light Processing (DLP) technique, or Stepped Optical Phased Array (SOPA) technique; and
   an Opto-Electronic subsystem, including:
      a plurality of lasers optically connected to the focusing lens through a first mixer, wherein:
         each laser is configured to transmit light, in sequence for a duration of time, to the first mixer;
         the first mixer is configured to generate an amplitude modulated optical waveform centered around the frequency $f_n$ for an $n^{th}$ laser and having a bandwidth of B represented by the formula $W(t)=\cos(2\pi(f_n-(B/2))t)+\cos(2\pi(f_n+(B/2))t)$; and
         the amplitude modulated optical waveform is beamed to the focusing lens and transmitted to the beam steering apparatus;
      a plurality of Avalanche Photo Diodes (APD) electrically connected to a second mixer and optically connected to the collection lens through a plurality of optical filters, wherein:
         each APD is optically connected to a corresponding optical filter and each optical filter is tuned to a wavelength of a different second harmonic generated;
         each APD is configured to receive reflection light through the corresponding optical filter and the collection lens, and convert the reflection light into a time varying voltage;
         the second mixer is configured to mix the time varying voltage from each APD to an intermediate frequency (IF) band by mixing with a signal represented by a function $\cos(2\pi f_{hmt})$, where "$f_{hn}$" denotes a mixing signal corresponding to the $n^{th}$ laser;
         the second mixer is configured to provide a voltage output to a first filter, which is configured to eliminate high frequency components so that only an image of the time varying voltage of the APDs around the IF remains; and
         the first filter is configured to provide an output to a low noise amplifier to amplify the output and provide an amplified output to a digitization subsystem; and
      the digitization subsystem, including a third mixer, an image filter, a sampler, an analog to digital converter, a segment spectrum calculator and an energy spectral density calculator, wherein:
         the third mixer is configured to receive the amplified output and the energy spectral density calculator is configured to generate an EF(f) function based on an output from the segment spectrum calculator provided by the analog to digital converter; and
         the EF(f) function represents an estimate of composite energy spectral density of all second harmonic generated and defined by a set of functions $E_n(f)$ where each "n" corresponds to one of the plurality of lasers;
      wherein the processor is configured to:
         fill gaps in the EF(f) function using a polynomial fitting function, spline function, analytic continuation technique, or a Whittaker-Shannon interpolation;
         generate M samples $E_1, E_2, \ldots, E_M$ of EA(f) at M frequencies where M is an integer $\geq N$, a number of the plurality of lasers; and
         provide the M samples $E_1, E_2, \ldots, E_M$ to the artificial intelligence subsystem;
      wherein the processor is configured to execute the artificial intelligence subsystem that generates a final decision output as to whether cancer is detected in a target area, wherein the artificial intelligence subsystem includes:
         a neural network comprising:
            a first neural network, wherein:
               the first neural network is a four layer feed forward neural network trained using a first set of data;
               the first neural network includes an input layer comprising input nodes, a first hidden layer comprising first hidden nodes, a second hidden layer comprising second hidden nodes, a first output layer comprising first output nodes;
               a number of input nodes is more than a number of the first hidden nodes, which is more than a number of the second hidden nodes, which is more than a number of the first output nodes;
               each node is configured to calculate a Sigmoid Function;
               the first neural network is configured to receive the M samples $E_1, E_2, \ldots, E_M$, each sample at one and only one input node of the first neural network, and generate a first decision output; and
               the first neural network is trained using the first dataset including first spectral data and corresponding BI-RADS classifications during a first cycle; and a second neural network, wherein:
  the second neural network includes a hidden layer and a second output layer;
  the second neural network is configured to receive the first decision output from the first output layer and generate a second decision output;
  the second neural network is trained using a second set of data during a second cycle after the first cycle, the second set of data including second spectral data and corresponding BI-RADS classifications as related to biopsy classifications, wherein:
    the second neural network is configured to pass output corresponding to the second set of data to a comparator configured to calculate an error metric based on the first decision output and the biopsy classification;
    an absolute value of the error metric is fed back during the second cycle to adjust node weights in the second neural network; and
    the comparator is only operational during the second cycle; and
  a rule-based logical reasoning algorithm wherein the rule-based logical reasoning algorithm:
    is configured to receive the second decision output and generate the final decision output based on a third set of data; and
    is a sequential decision algorithm, a cumulative threshold decision algorithm, a correlative coding decision algorithm, or a purge and develop algorithm.

2. A device comprising:
a processor;
a memory which stores an artificial intelligence subsystem;
a display;
a beam steering apparatus configured to steer a focusing lens and a collection lens over an angle to scan an active area; and
an Opto-Electronic subsystem, including:
  a plurality of lasers optically connected to the focusing lens through a first mixer;
  a plurality of Avalanche Photo Diodes (APD) electrically connected to a second mixer and optically connected to the collection lens through a plurality of optical filters; and
  a digitization subsystem, including a third mixer, an image filter, a sampler, an analog to digital converter, a segment spectrum calculator and an energy spectral density calculator, wherein the processor is configured to provide M samples $E_1, E_2, \ldots, E_M$ from the digitization subsystem to the artificial intelligence subsystem;
wherein the processor is configured to execute the artificial intelligence subsystem that generates a final decision output as to whether cancer is detected in a target area, wherein the artificial intelligence subsystem includes:
  a neural network comprising:
    a first neural network, wherein:
      the first neural network is a four layer feed forward neural network trained using a first set of data;
      the first neural network includes an input layer comprising input nodes, a first hidden layer comprising first hidden nodes, a second hidden layer comprising second hidden nodes, a first output layer comprising first output nodes;
      a number of input nodes is more than a number of the first hidden nodes, which is more than a number of the second hidden nodes, which is more than a number of the first output nodes;
      each node is configured to calculate a Sigmoid Function;
      the first neural network is configured to receive the M samples $E_1, E_2, \ldots, E_M$, each sample at one and only one input node of the first neural network, and generate a first decision output; and
      the first neural network is trained using the first dataset including first spectral data and corresponding BI-RADS classifications during a first cycle; and
    a second neural network, wherein:
      the second neural network includes a hidden layer and a second output layer;
      the second neural network is configured to receive the first decision output from the first output layer and generate a second decision output;
      the second neural network is trained using a second set of data during a second cycle after the first cycle, the second set of data including second spectral data and corresponding BI-RADS classifications as related to biopsy classifications, wherein:
        the second neural network is configured to pass output corresponding to the second set of data to a comparator configured to calculate an error metric based on the first decision output and the biopsy classification;
        an absolute value of the error metric is fed back during the second cycle to adjust node weights in the second neural network; and
        the comparator is only operational during the second cycle; and
      a rule-based logical reasoning algorithm wherein the rule-based logical reasoning algorithm:
        is configured to receive the second decision output and generate the final decision output based on a third set of data; and
        is a sequential decision algorithm, a cumulative threshold decision algorithm, a correlative coding decision algorithm, or a purge and develop algorithm.

3. The device of claim 2, wherein:
each laser is tuned to a different frequency in a range $[\lambda_L, \lambda_U]$ or $[f_L, f_U]$ where $\lambda_L$=650 nm to $\lambda_U$=1350;
each laser is configured to transmit light, in sequence for a duration of time, to the first mixer;
the first mixer is configured to generate an amplitude modulated optical waveform centered around the frequency $f_n$ for an $n^{th}$ laser and having a bandwidth of B represented by the formula $W(t)=\cos(2\pi(f_n-(B/2))t)+\cos(2\pi(f_n+(B/2))t)$; and
the amplitude modulated optical waveform is beamed to the focusing lens and transmitted to the beam steering apparatus.

4. The device of claim 3, wherein:
each APD is optically connected to a corresponding optical filter and each optical filter is tuned to a wavelength of a different second harmonic generated;

each APD is configured to receive reflection light through the corresponding optical filter and the collection lens, and convert the reflection light into a time varying voltage;

the second mixer is configured to mix the time varying voltage from each APD to an intermediate frequency (IF) band by mixing with a signal represented by a function $\cos(2\pi f_{hn}t)$, where "$f_{hn}$," denotes a mixing signal corresponding to the $n^{th}$ laser;

the second mixer is configured to provide a voltage output to a first filter, which is configured to eliminate high frequency components so that only an image of the time varying voltage of the APDs around the IF remains; and the first filter is configured to provide an output to a low noise amplifier to amplify the output and provide an amplified output to the digitization subsystem.

5. The device of claim 4, wherein:

the third mixer is configured to receive the amplified output and the energy spectral density calculator is configured to generate an EF(f) function based on an output from the segment spectrum calculator provided by the analog to digital converter; and the EF(f) function represents an estimate of composite energy spectral density of all second harmonic generated and defined by a set of functions $E_n(f)$ where each "n" corresponds to one of the plurality of lasers;

wherein the processor is configured to:

fill gaps in the EF(f) function using a polynomial fitting function, spline function, analytic continuation technique, or a Whittaker-Shannon interpolation; and generate the M samples $E_1, E_2, \ldots, E_M$ of EA(f) at M frequencies where M is an integer $\geq N$, a number of the plurality of lasers.

6. The device of claim 5, wherein the beam steering apparatus includes:

rotating mirrors connected to mechanical attenuators with electric motors and galvanometers, mirrors located between two piezoelectric actuators, non-flat mirrors, steering devices based upon the gradient of refractive index in a liquid crystal cell with electrically controlled birefringence, an optical phased array, or an electro-optic scanner where the deflection angle is voltage controlled.

* * * * *

UNITED STATES PATENT AND TRADEMARK OFFICE
CERTIFICATE OF CORRECTION

PATENT NO. : 11,129,577 B2
APPLICATION NO. : 15/274925
DATED : September 28, 2021
INVENTOR(S) : Michael Breneisen et al.

Page 1 of 1

It is certified that error appears in the above-identified patent and that said Letters Patent is hereby corrected as shown below:

On the Title Page

Item (54) and in the Specification, Column 1, Lines 1-3, In title, -- OPTICAL CANCER DETECTOR USING DEEP OPTICAL SCANNING AND MULTI LAYER NEURAL NETWORK -- should read -- CANCER DETECTOR USING DEEP OPTICAL SCANNING AND MULTILAYER NEURAL NETWORK --.

Signed and Sealed this
Ninth Day of November, 2021

Drew Hirshfeld
*Performing the Functions and Duties of the
Under Secretary of Commerce for Intellectual Property and
Director of the United States Patent and Trademark Office*